(12) United States Patent
Kim et al.

(10) Patent No.: US 8,784,911 B2
(45) Date of Patent: Jul. 22, 2014

(54) COMPOSITIONS FOR TREATMENT AND PREVENTION OF DIABETIC COMPLICATIONS USING *OSTEOMELES SCHWERINAE*

(75) Inventors: Jin Sook Kim, Seoul (KR); Dae Sik Jang, Daejeon (KR); Young Sook Kim, Daejeon (KR); Yun Mi Lee, Daejeon (KR); Joo-Hwan Kim, Daejeon (KR); Eunjin Shon, Daejeon (KR); Junghyun Kim, Seoul (KR); Chan-Sik Kim, Daejeon (KR); Dong Ho Jung, Daejeon (KR); Nan Hee Kim, Daejeon (KR); Nam-Hee Yoo, Daejeon (KR); Jun Lee, Jinju-si (KR)

(73) Assignee: Korea Institute of Oriental Medicine, Daejeon (KR)

( * ) Notice: Subject to any disclaimer, the term of this patent is extended or adjusted under 35 U.S.C. 154(b) by 89 days.

(21) Appl. No.: 13/381,493

(22) PCT Filed: Nov. 5, 2009

(86) PCT No.: PCT/KR2009/006491
§ 371 (c)(1),
(2), (4) Date: Dec. 29, 2011

(87) PCT Pub. No.: WO2011/055869
PCT Pub. Date: May 12, 2011

(65) Prior Publication Data
US 2012/0100233 A1 Apr. 26, 2012

(51) Int. Cl.
*A61K 36/73* (2006.01)

(52) U.S. Cl.
USPC ............................................. 424/765; 514/866

(58) Field of Classification Search
None
See application file for complete search history.

(56) References Cited

FOREIGN PATENT DOCUMENTS

| EP | 0117600 A1 | 9/1984 |
|----|------------|--------|
| JP | 06-009326 A | 1/1994 |

OTHER PUBLICATIONS

Lee et al. (2010) J. Sep. Sci. Mar 33 (4-5): 582-586.*
Li et al. (2004) J. Ethnopharmacology vol. 92, Issue 1, pp. 1-21.*
Wu et al. (2005) J. Agric Food Chem. 53(8): pp. 3167-3173.*
Bate-Smith, "Detection and identification of anthocyanidins formed from Leuco-Anthocyanins in Plant Tissues", Biochem J., 1954, 58: 122-125.
Hsieh, et al., "*Osteomeles schwerinae* C.K. Schneid. (rosaceae): a new recprd for the flora of Taiwan", Bot. Bull. Acad. Sin., 1996, 37(4): 281-285.
Louati, et al., "Flavonoids from *Eriobotrya japonica* (Rosaceae) growing in Tunisia", Biochemical Systematics and Ecology, 2003, 31: 99-101.

* cited by examiner

*Primary Examiner* — Terry A McKelvey
*Assistant Examiner* — Russell Fiebig
(74) *Attorney, Agent, or Firm* — Lucas & Mercanti, LLP

(57) ABSTRACT

The present invention relates to a treatment agent for diabetic complications, and a method for the treatment of diabetic complications using the same. The present invention confirmed that *Osteomeles schwerinae* extract and its fractions inhibited the generation of AGEs, the index for diabetic complications, inhibited the activation of aldose reductase, had anti-cataract activity, and had anti-oxidative activity. Thus, the present invention relates to a preventive and therapeutic agent for diabetic complications containing the said *Osteomeles schwerinae* extract and its fraction as an active ingredient.

4 Claims, 31 Drawing Sheets

Fig. 23
(a)
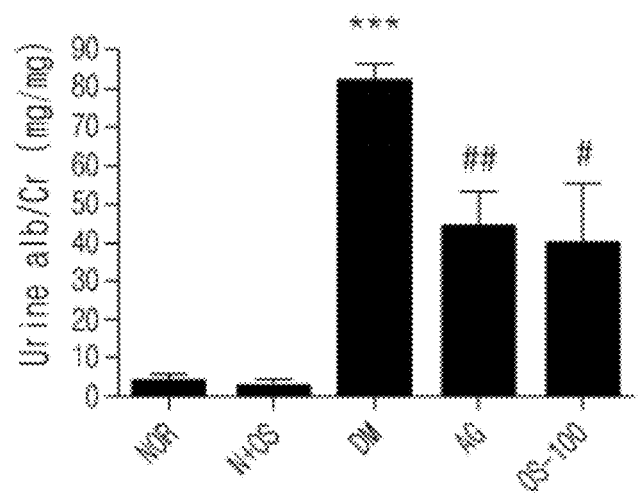
(b)
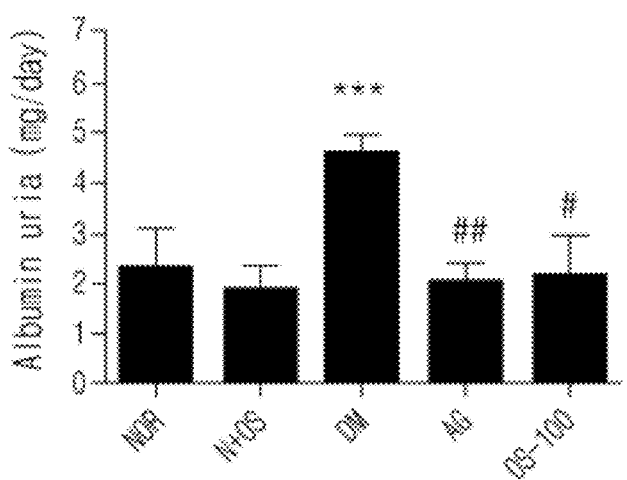

COMPOSITIONS FOR TREATMENT AND PREVENTION OF DIABETIC COMPLICATIONS USING *OSTEOMELES SCHWERINAE*

CROSS-REFERENCE TO RELATED APPLICATION

This application is a 371 of PCT/KR2009/006491, filed Nov. 5, 2009, the contents which are incorporated herein by reference.

BACKGROUND OF THE INVENTION

1. Field of the Invention

The present invention relates to *Osteomeles schwerinae* extract and the systematic fractions thereof which can be used as a pharmaceutical composition for the prevention and treatment of diabetic complications, and can be applied to a functional food as well.

2. Description of the Related Art

Diabetes is one of the critical adult diseases drawing our attention world-widely. Recently prevalence rate of diabetes reaches 10% in Korea, which has been growing along with the rapid growth of economy. The number of diabetes patients counts more than 240,000,000 over the world and is expected to reach 380,000,000 in 2025. It was presumed by JAMA, USA, in 2009 that 60% of the expected total diabetes would be reported in Asia. The time of onset of diabetes is tended to be earlier now, which seems to be largely the group of middle age. As life-time is extended, it is very hard to avoid complications. For instance, after 10-20 years from the onset of diabetes, almost every body organ is damaged to cause diabetic retinopathy, diabetic cataract, diabetic nephropathy, diabetic neuropathy, heart disease, cancer, and osteoporosis, etc. Chronic diabetic nephropathy requires hemodialysis and can be a critical reason of end stage renal disease. Diabetic cataract and diabetic retinopathy cause sight loss and even lead to death. In USA, the major reason of sight loss in the age group of 25-74 is diabetes. For example, 60% of diabetics lose their eye sight 15-20 years after the onset. Therefore, only if the occurrence of complications is postponed 5-10 years, the quality of life of a diabetic and his family will be totally different, affecting the national budget itself.

The mechanisms that cause diabetic complications are explained by nonenzymatic glycation of protein, polyol pathway, and oxidative stress, etc.

Nonenzymatic glycation of protein indicates condensation reaction of reducing sugar and amino acid group such as lysine residue of protein, which is Maillad reaction, without being mediated by enzyme. As a result of this reaction, advanced glycation endproducts (AGEs) are generated. Nonenzymatic glycation of protein is explained in more details: (1) amino acid group such as lysine residue of protein is reacted with aldehyde or ketone of reducing sugar without enzyme activity, which is nucleophilic addition, to produce the early stage product schiff base, and then ketoamine adducts residing close to the schiff base are reacted each other by condensation to produce reversible Amadori type early glycation products; and (2) when hyperglycemia status is longer, the reversible Amadori type early glycation products are not degraded and only rearranged to produce irreversible advanced glycation endproducts. The generated irreversible advanced glycation endproducts are conjugated or cross-linked with protein or lipid, leading to the generation of irreversible glycoprotein or glycolipid.

Unlike the reversible Amadori type early glycation product, the irreversible advanced glycation endproduct is not degradated once it is generated, even when the blood glucose level is recovered to normal, and is accumulated in tissues as long as the protein or lipid to which the advanced glycation endproduct is conjugated exists, resulting in abnormal changes in structure and function of tissues to cause complications (Vinson, J. A. et al., 1996, *J. Nutritional Biochemistry* 7: 559-663; Smith, P. R. et al., 1992, *Eur. J. Biochem.*, 210: 729-739).

For example, glycated albumin, one of the advanced glycation endproducts generated by the reaction between glucose and many kinds of proteins, is a critical cause of chronic diabetic nephropathy. Glycated albumin can be introduced into glomerular cells more easily than normal albumin. High concentration of glucose stimulates mesangium cells to increase extracellular matrix synthesis. Because of excessive glycated albumin introduced therein and increased extracellular matrix, glomerular fibrosis is induced. By such mechanism, glomerulus is continuously damaged, and at last extreme care such as hemodialysis or organ transplantation is required. As chronic diabetes continues, collagen is conjugated with the advanced glycation endproduct in arterial wall and also basement membrane protein is conjugated with the advanced glycation endproduct in glomerulus, which are accumulated in tissues (Brownlee, M., et al., 1986, *Sciences*, 232, 1629-1632).

Such nonenzymatic glycation of protein induces glycosylation of basement membrane, plasma albumin, lens protein, fibrin, and collagen, and the advanced glycation endproduct generated thereby causes abnormal changes in the structure and functions of tissues, leading to chronic diabetic complications such as diabetic retinopathy, diabetic cataract, diabetic nephropathy, and diabetic neuropathy.

Under the condition of hyperglycemia, when the advanced glycation endproduct is produced, lipid metabolism disorder is induced and at the same time defense system against toxic oxygen free radical is weakened to cause oxidative stress (Yokozawa, T., et al, 2001, *J. of Trad. Med.*, 18: 107-112). So, nonenzymatic glycation of protein is closely related to oxidative stress mechanism.

Polyol pathway is the process composed of the following steps: (1) Aldose or ketose is reduced by aldose reductase (AR) to generate sorbitol; and (2) The sorbitol is oxidized by dehydrogenase to produce fructose. In normal condition, aldose reductase exhibits very low affinity to glucose. However, under hyperglycemia condition, aldose reductase, the first enzyme of polyol pathway, is over-activated, and thus excessive blood glucose is converted to sorbitol and fructose, which are accumulated in tissues with breaking the balance of osmotic pressure, resulting in complications. That is, increased osmotic pressure drags moisture, leading to diabetic retinopathy, diabetic cataract, and diabetic neuropathy (Diabetes, Kim, et al., Korean Diabetes Association, Korea Medical Book Publisher, 483; Soulis-Liparota, T., et al., 1995, *Diabetologia*, 38: 357-394).

It was reported that the advanced glycation endproduct activates aldose reductase (AR), the main enzyme of polyol pathway, in human microvascular endothelial cells (Nakamura, N., et al., 2000, *Free Radic Biol. Med.*, 29: 17-25). At this time, the speed of nonenzymatic glycation of fructose is approximately 10 times as fast as glucose. So, when high concentration of fructose is conjugated with protein, the generation of the advanced glycation endproduct is accelerated.

The mechanisms of nonenzymatic glycation of protein, polyol pathway, and oxidative stress are all connected to cause diabetic complications. So, it is very important to inhibit the generation of advanced glycation endproduct to postpone, prevent or treat diabetic complications (Brownlee, M., et al., 1988, *N. Engl. Med.,* 318, 1315-1321).

Aminoguanidine, the synthetic protein glycosylation inhibitor, is nucleophilic hydrazine, which is conjugated with Amadori product to intervene cross-linking of protein, resulting in the inhibition of the generation of advanced glycation endproduct, by which it can postpone or prevent the progress of diabetic complications (Brownlee, M., et al., 1986, *Sciences,* 232, 1629-1632; Edelstein, D. et al., 1992, *Diabetes,* 41, 26-29). Therefore, aminoguanidine has been known as the promising synthetic medicine for the prevention and treatment of diabetic complications, and thus the third phase clinical test has been completed. However, the clinical test of aminoguanidine has been stopped because of its toxicity observed during the long term administration. Accordingly it is an urgent request to develop a safer and more effective natural drug.

Thus, the present inventors have tried to develop a composition for the treatment of diabetic complications using natural substances and at last the inventors completed this invention by confirming that *Osteomeles schwerinae* extract and its fractions have anti-diabetes, anti-aging and anti-cancer effects.

SUMMARY OF THE INVENTION

It is an object of the present invention to provide a composition for the prevention, postponement, and treatment of diabetic complications such as lens fiber degeneration, pathologic abnormalities in retina and kidney, etc, by inhibiting the generation of advanced glycation endproduct, one of the major causes of diabetic complications, and the excessive activity of aldose reductase with demonstrating anti-oxidative effect, and a method for the treatment of diabetic complications using the same.

It is another object of the present invention to provide a composition for the prevention or postponement of aging, and the prevention or treatment of cancer, prepared based on the consideration that the advanced glycation endproduct and oxidative stress can be a reason of aging and cancer, and a method for the prevention of aging using the same.

To achieve the above objects, the present invention provides a composition for the treatment of diabetic complications and for the prevention or postponement of aging comprising *Osteomeles schwerinae* extract extracted by using alcohol, water or the mixture thereof, and fractions thereof, fractionated with hexane, ethyl acetate, butanol, and water stepwise.

The present invention also provides a method for the prevention and treatment of diabetic complication and for the prevention of aging using the said extract and fractions.

The present invention further provides a functional health food for the prevention and improvement of diabetic complications, a pharmaceutical composition and a functional health food for the prevention or postponement of aging, comprising the said extract and fractions.

ADVANTAGEOUS EFFECT

*Osteomeles schwerinae* extract is a natural extract which is safe without toxicity, compared with the conventional therapeutic agents for diabetic complications, and very effective in treating diabetic complications. Therefore, *Osteomeles schwerinae* extract can be effectively used for the preparation of a pharmaceutical composition and a functional health food for the prevention, postponement and treatment of diabetic complications.

BRIEF DESCRIPTION OF THE DRAWINGS

The application of the preferred embodiments of the present invention is best understood with reference to the accompanying drawings, wherein:

FIG. 23 is a set of graphs illustrating the changes of renal function markers in type I diabetes animal model after the treatment of *Osteomeles schwerinae* extract.

DESCRIPTION OF THE PREFERRED EMBODIMENTS

Figure 1:
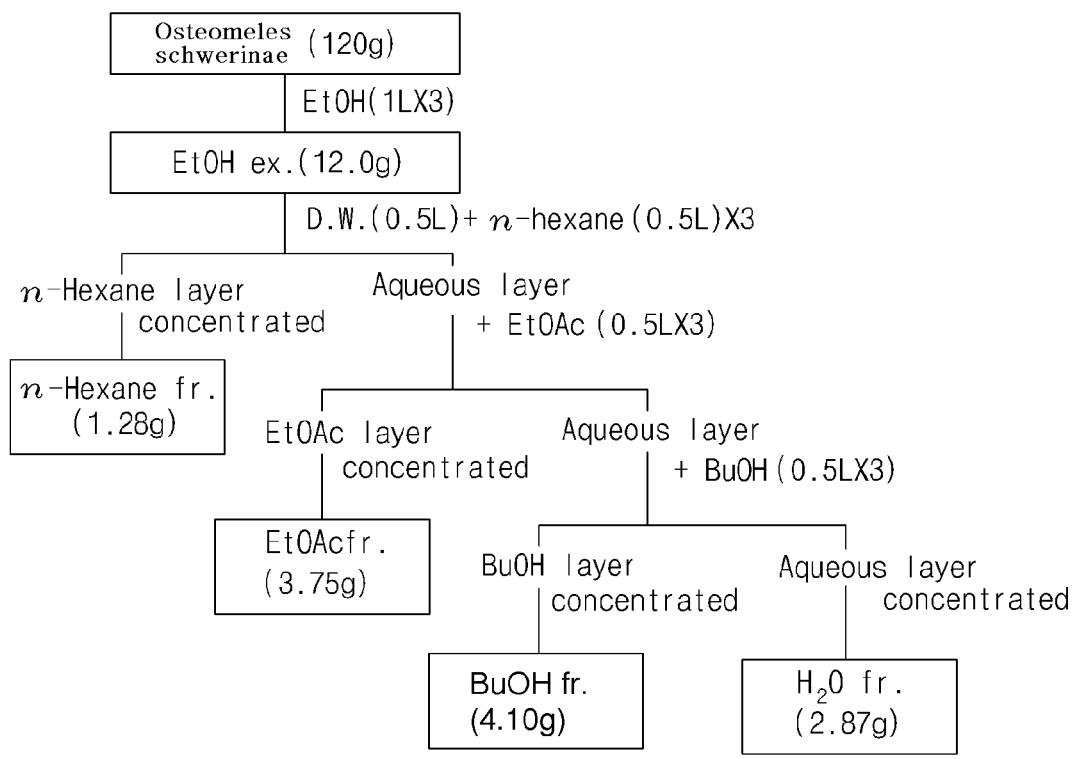
FIG. 1 is a diagram illustrating the extraction and systematic fractionation of *Osteomeles schwerinae*.

Hereinafter, the present invention is described in detail.

The present invention provides a composition for the prevention and treatment of diabetic complications, comprising *Osteomeles schwerinae* extract or its fractions as an active ingredient.

Diabetic complications are the symptoms occurring when diabetes progresses for a long time, which thus are generated by diabetes but are completely different disease from diabetes. So, the standards of judgment for diabetic complications and diabetes are different from each other, and thus the treatment agent for diabetic complications is totally different from the one used for diabetes.

Diabetic complications are caused by advanced glycation endproducts (AGEs) and abnormal activity of aldose reductase and increased oxidative stress. Therefore, the effect of a therapeutic agent candidate for diabetic complications can be evaluated by measuring the advanced glycation endproducts, aldose reductase activity and anti-oxidative activity. Diabetic complications are exemplified by diabetic retinopathy, diabetic cataract, diabetic nephropathy, and diabetic neuropathy. So, the effect of the therapeutic agent candidate can be proved by investigating the inhibition of diabetic retinopathy, diabetic cataract, diabetic nephropathy, and diabetic neuropathy.

In this invention, the present inventors confirmed that *Osteomeles schwerinae* extract and its fractions have therapeutic effect on diabetic complications and also confirmed that they have inhibitory effect of advanced glycation endproduct generation and aldose reductase activity along with anti-oxidative effect. In addition, the inventors confirmed that *Osteomeles schwerinae* extract has ex vivo anti-cataract effect. The present inventors also confirmed that *Osteomeles schwerinae* extract is effective on the prevention, postponement, and treatment of diabetic retinopathy, diabetic cataract, diabetic nephropathy, and diabetic neuropathy in type 1 and type II diabetic animal models (FIG. 23-FIG. 40). Therefore, the present inventors confirmed via in vitro, ex vivo, and in vivo animal model experiments that *Osteomeles schwerinae* extract and its fractions are promising candidates for the composition for the prevention, postponement, and treatment of diabetic complications.

*Osteomeles schwerinae* used in this invention is a deciduous shrub belonging to Roseceae. The height is 1-3 m, and small branches are thin and weak and slightly bended with reddish brown or brownish gray. Its young twigs are full of light gray hairs and they lose them as they grow. The perennial branches are dark brown. The pharmaceutical effect of this plant has been known as smooth and clams. It is effective in dissipating heat and detoxifying, astriction and antidiarrhea, dispelling wind and eliminating damp, sores and pyogenic infections, swollen and painful throat, dysenteric disorder, diarrhea, bleeding before defecation, prolapsed of genitalia, pain wind-damp and arthralgia, etc (Zhong Hua Ben Cao, Shanghai Kexue JiShu ChuBansh, Vol. 4, 2677; ISBN 7-5323-5106-8/R. 1287).

The composition and physiological activity of *Osteomeles schwerinae* have not been reported, yet.

For the *Osteomeles schwerinae* extract of the present invention, the whole plant of *Osteomeles schwerinae* can be used. Young and small twigs, leaves, or seeds are preferred, but other parts of the plant can be used as well.

The *Osteomeles schwerinae* extract of the present invention can be prepared by the conventional extraction method well known to those in the art such as ultrasonic extraction, filtration, and reflux extraction.

The extract of the present invention can be extracted from dried *Osteomeles schwerinae* plant by using water, $C_1$~$C_4$ lower alcohol, or the mixed solvent thereof. At this time, the lower alcohol is preferably methanol or ethanol.

The volume of the solvent used herein is 1-10 times the volume of the extract, or preferably 1-5 times the volume. The preferable amount of the solvent is 1-10 times the amount of dried *Osteomeles schwerinae*, and more preferably 1-5 times the amount.

The fractions of the present invention were prepared from the extract of the invention. First, hexane fraction was obtained by separating hexane layer after adding water and hexane to the residue obtained by eliminating solvent from the extract of the present invention. Then, ethyl acetate fraction was obtained by separating ethyl acetate layer after adding ethyl acetate to the water layer. After eliminating ethyl acetate layer, butanol was added thereto to separate butanol fraction. After eliminating butanol layer, water layer was lastly obtained.

To analyze the inhibitory effect on the generation of advanced glycation endproduct, which can be used as the index of diabetic complications and the treatment effect thereof, the present inventors measured the binding degree of fructose and glucose by using BSA (bovine serum albumin). As the positive control, aminoguanidine known to have excellent inhibitory effect on advanced glycation endproduct was used. In the experimental group treated with *Osteomeles schwerinae* or its fractions, the extract or its fractions demonstrated higher effect than that of aminoguanidine (Table 2, FIG. 3-FIG. 8).

To confirm the functions of *Osteomeles schwerinae* extract and its fractions more accurately, the present inventors investigated if they could inhibit the cross-linking between advanced glycation endproducts and collagen or if they could break the cross-linking established already between advanced glycation endproducts and collagen.

The *Osteomeles schwerinae* extract and its fractions of the present invention were compared with aminoguanidine known as the AGEs cross-linker inhibitor. As a result, the *Osteomeles schwerinae* extract and its fractions obtained from leaves, small twigs, and seeds of the plant were confirmed to have excellent cross-linker inhibitory effect (FIGS. 9, 11, 13, 15 and 17).

The *Osteomeles schwerinae* extract and its fractions of the present invention were also compared with ALT-711 known as the AGEs cross-linker breaker (Alteon Inc., Ramsey, N.J.), and as a result, the *Osteomeles schwerinae* extract and its fractions obtained from leaves, small twigs, and seeds of the plant were confirmed to have excellent AGEs cross-linker breaking effect (FIGS. 10, 12, 14, 16 and 18).

Therefore, the present inventors confirmed that *Osteomeles schwerinae* extract and its fractions inhibited advanced glycation endproduct generation and cross-linking with other proteins, suggesting that the extract and its fractions of the present invention have excellent preventive and therapeutic effect on diabetic complications.

The present inventors further investigated if *Osteomeles schwerinae* extract and its fractions could inhibit the activity of aldose reductase which is another index for diabetic complications. At this time, 3,3-tetramethylene glutaric acid was used as the comparative control. As a result, the *Osteomeles schwerinae* extract and its fractions of the present invention were confirmed to have excellent aldose reductase inhibitory effect, compared with the conventional aldose reductase inhibitors (see Table 6).

Anti-oxidative effect of *Osteomeles schwerinae* extract and its fractions was investigated by measuring free radicals by DPPH method. As a result, the *Osteomeles schwerinae* extract and its fractions of the present invention demonstrated as high as or higher anti-oxidative effect than vitamin C, vitamin E or BHT (butylated hydroxytoluene) used as the positive control (see Table 7).

As explained hereinbefore, it was confirmed that the *Osteomeles schwerinae* extract and its fractions of the present invention have excellent effects on the inhibition of AGEs generation, which is a reason of diabetic complications and at the same time an index to evaluate the treatment effect for diabetic complications, the inhibition of cross-linking with other proteins, the inhibition of aldose reductase activity, and the anti-oxidation, so that they can be used as a composition for the prevention, postponement and treatment of diabetic complications.

Figure 19:
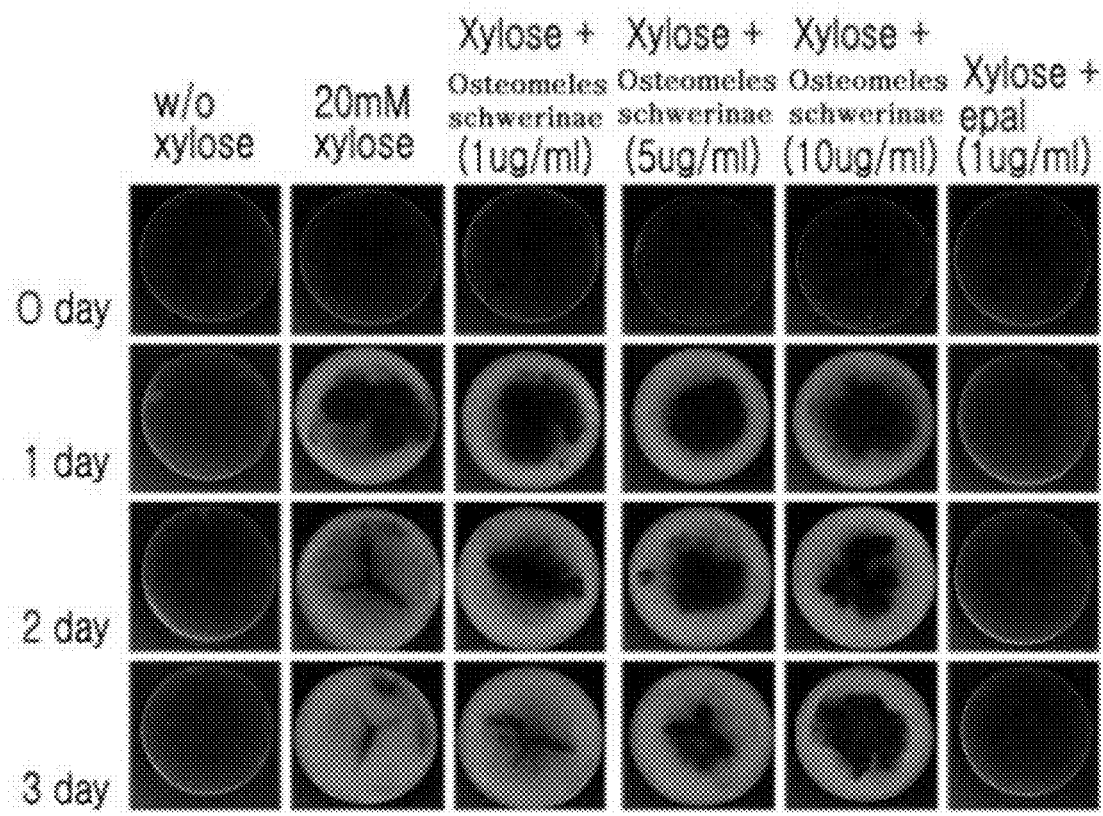
FIG. 19 is a set of photographs illustrating the anti-cataract effect of *Osteomeles schwerinae* extract in the ex vivo mouse lens.
Figure 20:
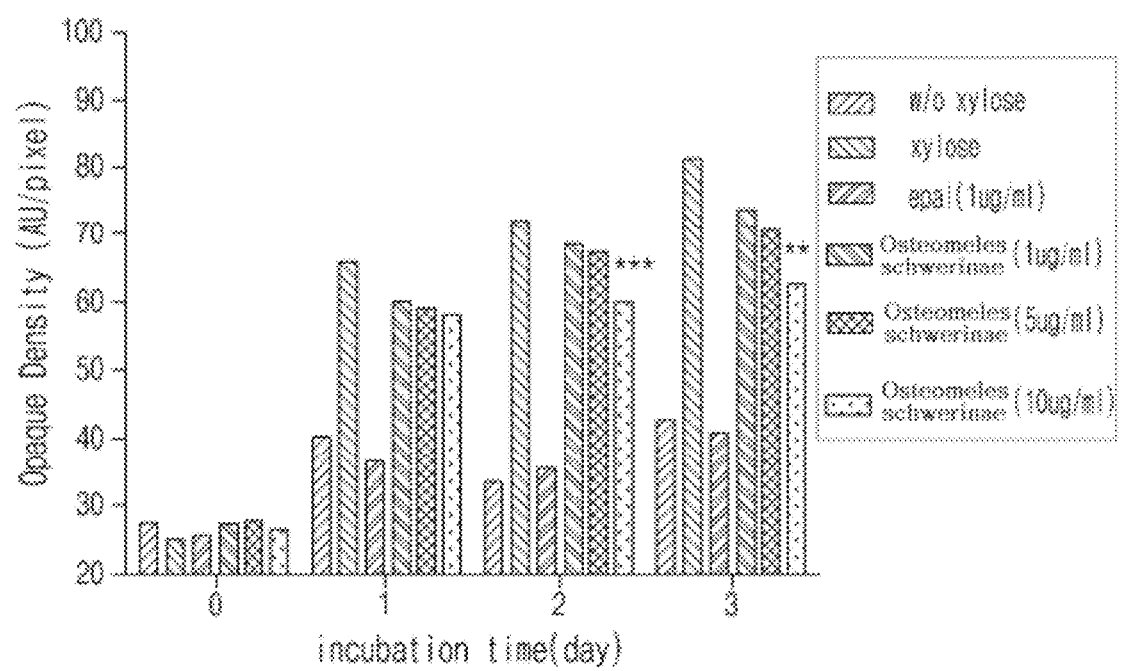
FIG. 20 is a graph illustrating the anti-cataract effect of *Osteomeles schwerinae* small twig/leaf extract in the ex vivo mouse lens.
Figure 21:
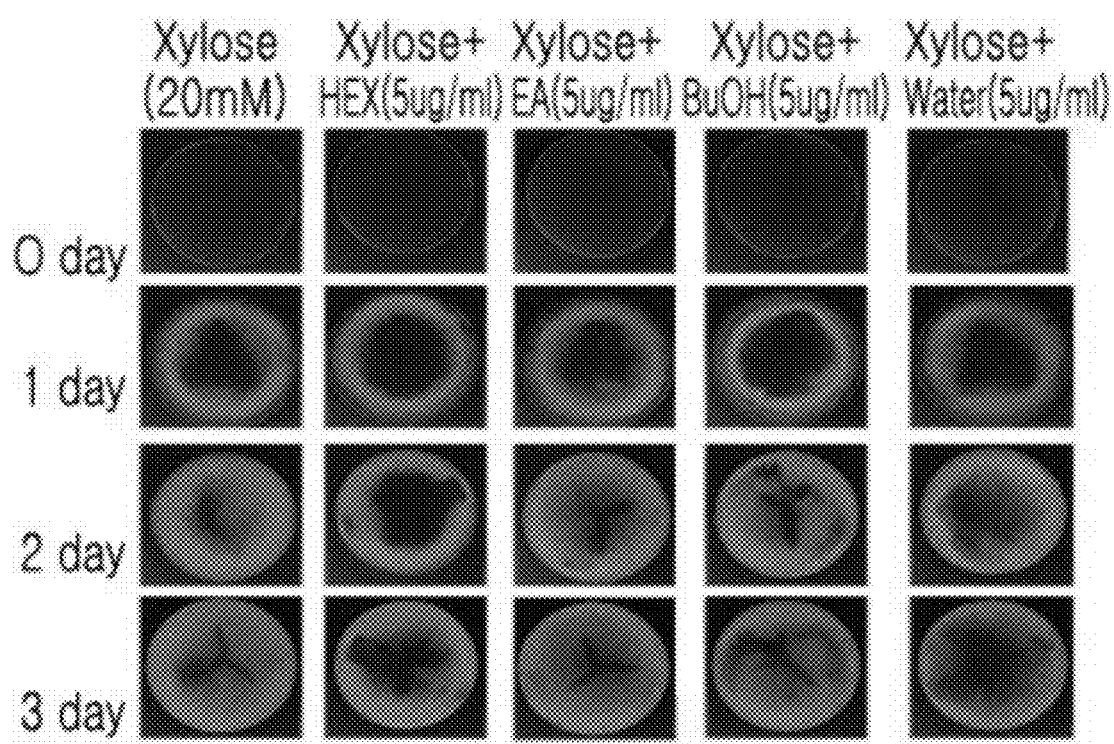
FIG. 21 is a set of photographs illustrating the anti-cataract effect of fractions of *Osteomeles schwerinae* small twig/leaf extract in the ex vivo mouse lens.
Figure 22:
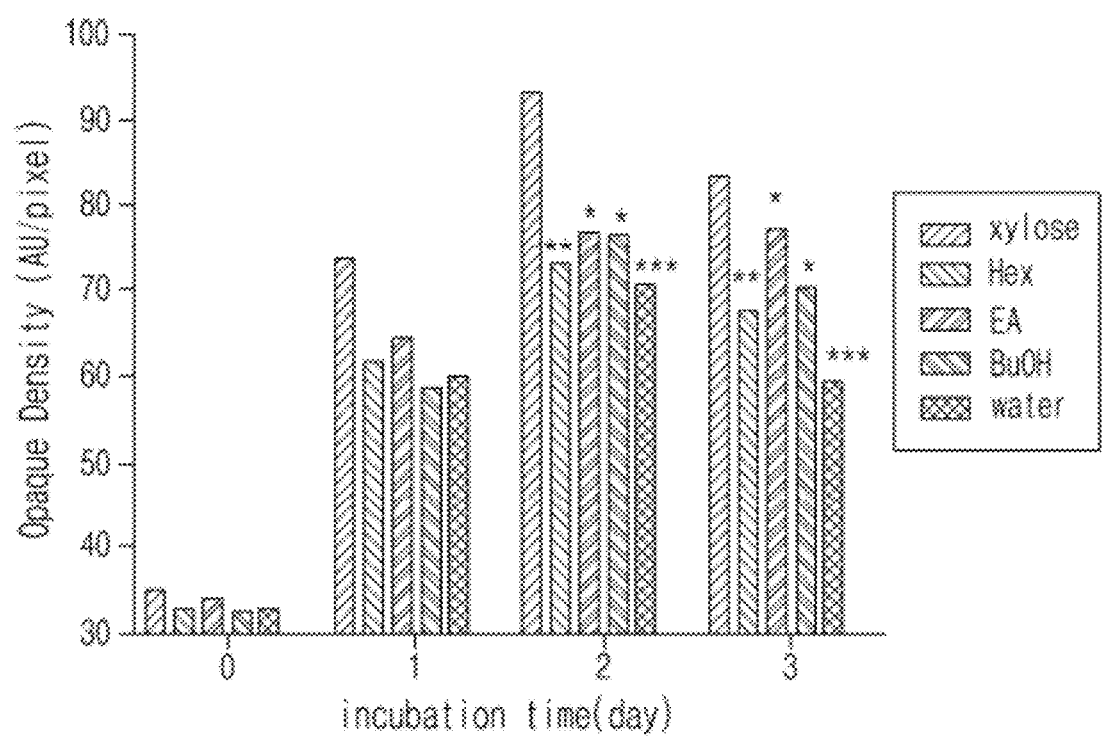
FIG. 22 is a graph illustrating the anti-cataract effect of fractions of *Osteomeles schwerinae* small twig/leaf extract in the ex vivo mouse lens.
Figure 24:
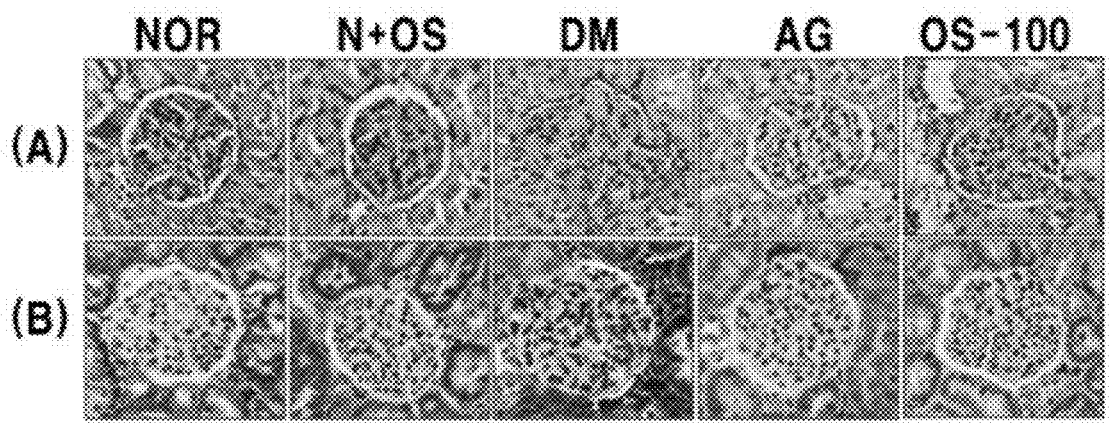
FIG. 24 is a set of photographs illustrating the histological renal changes in type I diabetes animal model after the treatment of *Osteomeles schwerinae* extract; (A): PAS (periodic acid shiff) staining, (B): Masson's trichrome staining.
Figure 25:
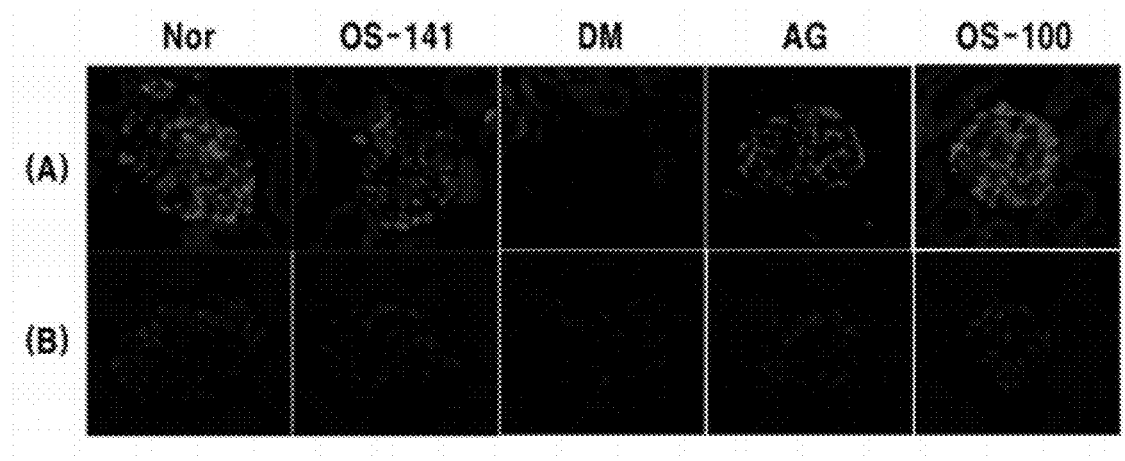
FIG. 25 is a set of photographs illustrating the changes of podocyte loss in type I diabetes animal model after the treatment of *Osteomeles schwerinae* extract; (A): Synatopodin staining, (B): WT-1 staining.
Figure 26:
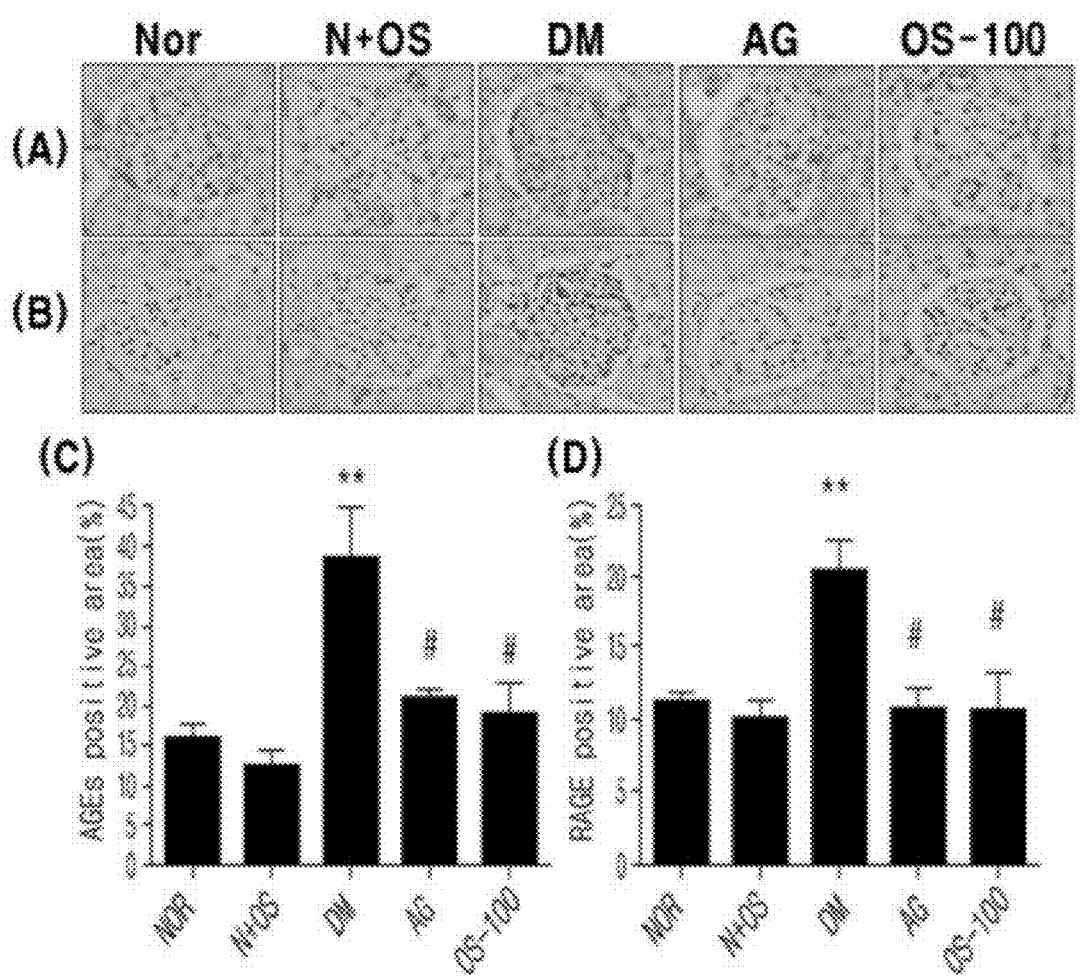
FIG. 26 is a set of photographs and graphs illustrating the changes of expression patterns of advanced glycation endproducts (AGEs) (A, C) and advanced glycation endproduct receptor (RAGE protein) (B, D) in type I diabetes animal model after the treatment of *Osteomeles schwerinae* extract.
Figure 27:
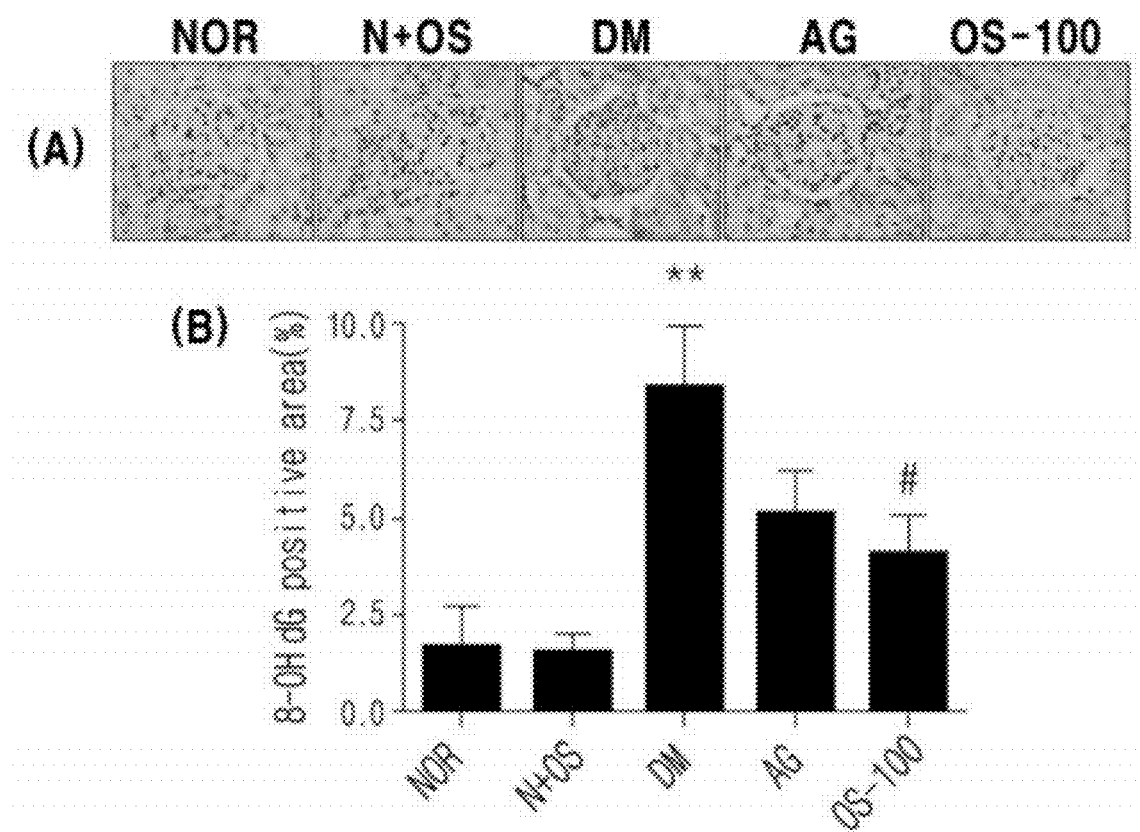
FIG. 27 is a set of photographs and a graph illustrating the anti-oxidative effect of *Osteomeles schwerinae* extract investigated in type I diabetes animal model.
Figure 28:
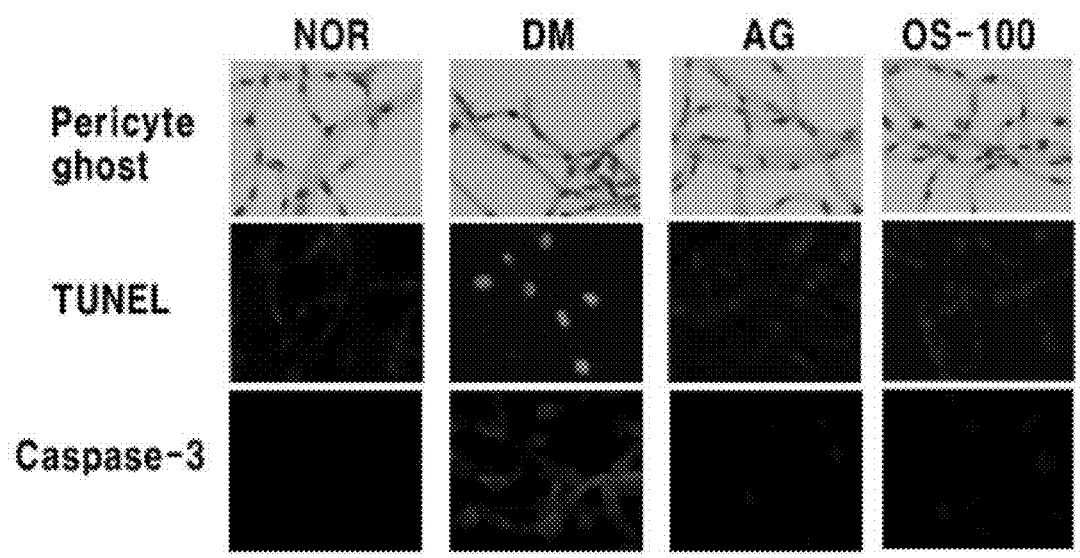
FIG. 28 is a set of photographs illustrating the preventive effect of *Osteomeles schwerinae* extract on the damages of retinal vascular pericytes and vascular endothelial cells in type I diabetes animal model.
Figure 29:
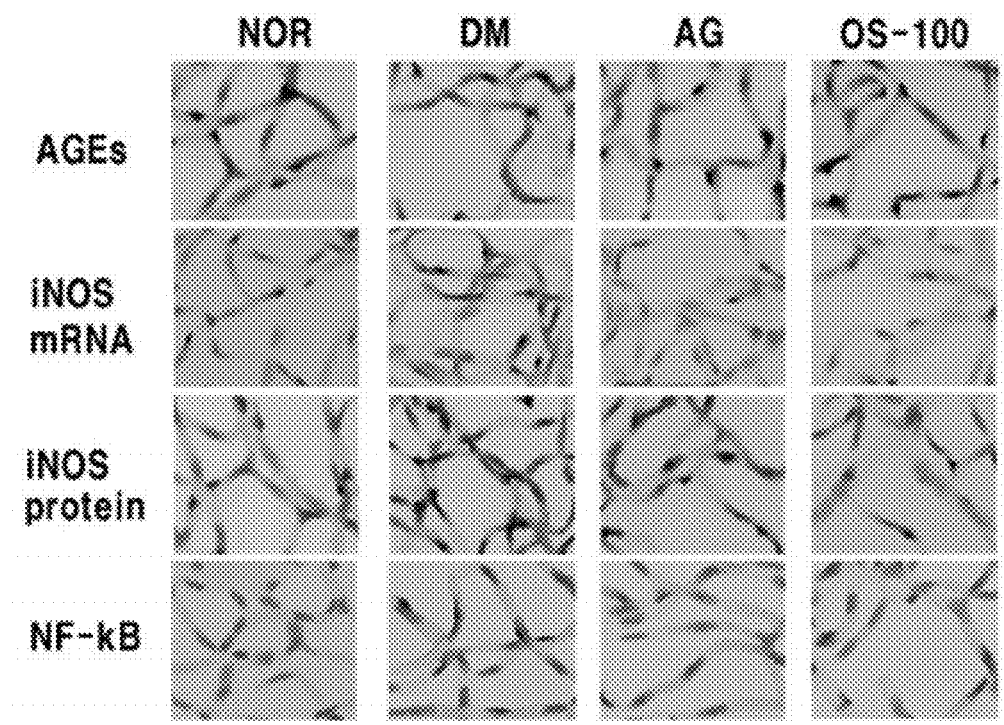
FIG. 29 is a set of photographs illustrating the changes of expression patterns of AGEs, iNOS (inducible nitric oxide synthase) and NF-κB involved in retinal vascular cell damage in type I diabetes animal model after the treatment of *Osteomeles schwerinae* extract.
Figure 30:
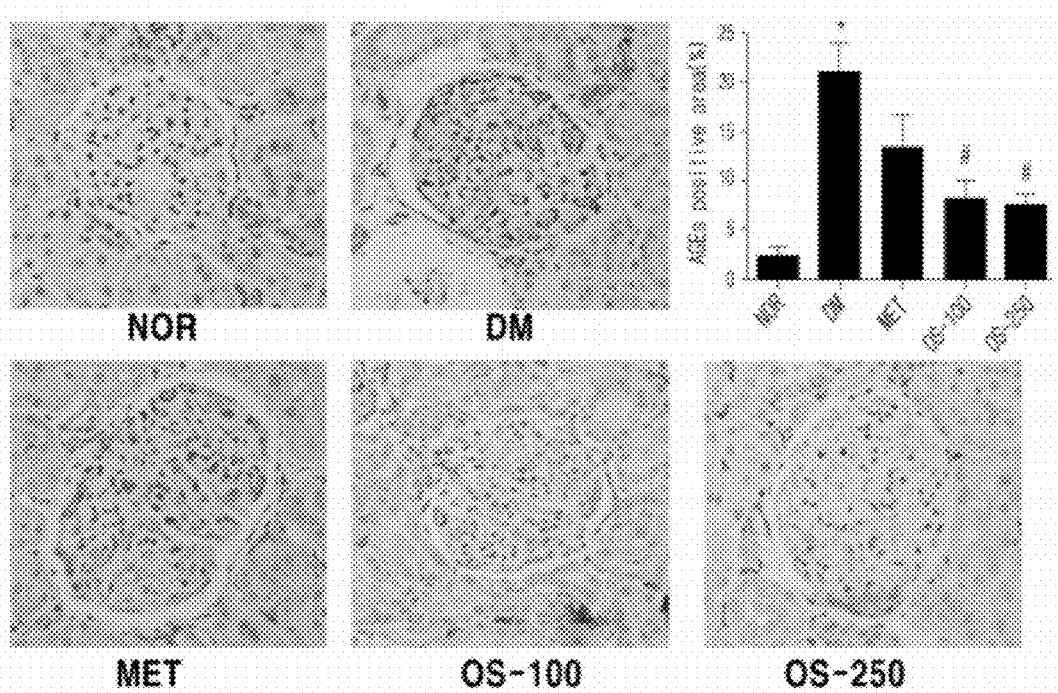
FIG. 30 is a set of photographs and a graph illustrating the AGEs inhibition effect of *Osteomeles schwerinae* extract in the kidney of type II diabetes animal model (SDT).
Figure 31:
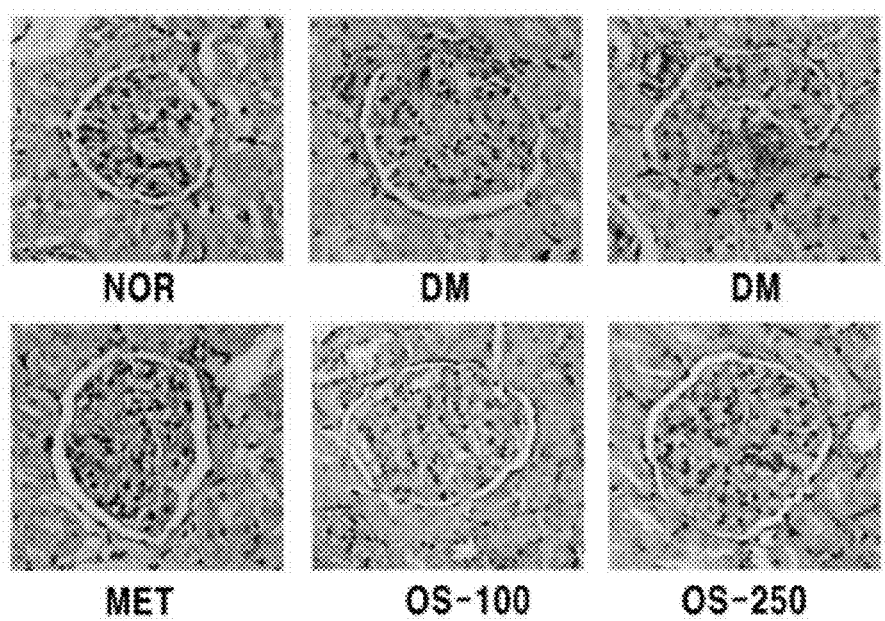
FIG. 31 is a set of photographs illustrating the PAS-stained kidney of type II diabetes animal model after the treatment of *Osteomeles schwerinae* extract.

To confirm the effect of *Osteomeles schwerinae* extract and its fractions on treating diabetic complications in reality, the inventors performed ex vivo experiments. Particularly, the inventors investigated the inhibitory effect of *Osteomeles schwerinae* extract and its fractions on diabetic cataract that is one of the most representative diabetic complications. Diabetic cataract was induced by xylose, followed by the treatment with *Osteomeles schwerinae* extract and its fractions. As a result, significant diabetic cataract treating effect of the extract and its fractions was confirmed (FIG. 19 and FIG. 20 illustrate the effect of *Osteomeles schwerinae* extract, and FIG. 21 and FIG. 22 illustrate the effect of the fractions each obtained by using hexane, ethyl acetate, butanol, and water from the *Osteomeles schwerinae* extract). In particular, *Osteomeles schwerinae* extract demonstrated excellent anti-diabetic cataract effect at the concentration of 10 μg/ml (FIG. 19 and FIG. 20), and those 4 fractions also showed excellent anti-diabetic cataract effect at the concentration of 5 μg/ml (FIG. 21 and FIG. 22). In addition, the *Osteomeles schwerinae* extract and its fractions of the present invention demonstrated excellent preventive and treating effect on diabetic cataract, retinopathy, and nephropathy in type I diabetes animal model induced by streptozotocin (STZ) and in type II diabetes animal model, the SDT (spontaneous diabetic torii) rat. The above effect of the *Osteomeles schwerinae* extract and its fractions of the present invention was greater than that of the positive controls, aminoguanidine (type I diabetes model) and metformin (type II diabetes model) (FIGS. 23-40).

*Osteomeles schwerinae* extract was treated to the normal group animals (SD rats) once a day for 8 weeks at the dose of 200 mg/kg/day. During the administration, no rats were dead. Blood ALT and AST levels (indexes for liver function test) of the animals were in the normal range, suggesting that livers of the animals were not affected by the treatment (see Table 9).

The pharmaceutical composition of the present invention contains the *Osteomeles schwerinae* extract and its fractions of the present invention at the concentration of 0.1-99.9 weight % by the total weight of the composition and can additionally include any pharmaceutically acceptable carrier, excipient, or diluent.

The pharmaceutical composition of the present invention can be prepared for oral or parenteral administration by mixing with generally used diluents or excipients such as fillers, extenders, binders, wetting agents, disintegrating agents and surfactant. Solid formulations for oral administration are tablets, pills, powders, granules and capsules. These solid formulations are prepared by mixing *Osteomeles schwerinae* extract of the present invention with one or more suitable excipients such as starch, calcium carbonate, sucrose or lactose, gelatin, etc. Except for the simple excipients, lubricants, for example magnesium stearate, talc, etc, can be used. Liquid formulations for oral administration are suspensions, solutions, emulsions and syrups, and the above-mentioned formulations can contain various excipients such as wetting agents, sweeteners, aromatics and preservatives in addition to generally used simple diluents such as water and liquid paraffin. Formulations for parenteral administration are sterilized aqueous solutions, water-insoluble excipients, suspensions, emulsions, lyophilized preparations and suppositories. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerogelatin, etc.

The applicable subject of the pharmaceutical composition of the present invention is vertebrates and preferably mammals and more preferably such test animals as rats, mice, rabbits, guinea pigs, hamsters, dogs and cats, and most preferably apes such as chimpanzees, gorillas and human beings.

The pharmaceutical composition of the present invention can be treated by oral or parenteral administration. Parenteral administration is preferably exemplified by external skin application, rectal administration, intravenous injection, intramuscular injection, hypodermic injection, intrauterine injection or intracerebroventricular injection. However, external skin application is most preferred.

The effective dosage of the pharmaceutical composition of the present invention can be determined according to weight, age, gender, health condition, diet, administration frequency, administration method, excretion and severity of disease. The dosage of *Osteomeles schwerinae* extract is 0.01~1000 mg/kg per day, preferably 30~500 mg/kg per day, and more preferably 50~300 mg/kg per day, and administration frequency is preferably 1~6 times a day.

The pharmaceutical composition of the present invention can be administered alone or together with surgical operation, radio therapy, hormone therapy, chemo-therapy and biological regulators.

The present invention also provides a functional health food for the prevention and improvement of diabetic complications, comprising *Osteomeles schwerinae* extract and its fractions as an active ingredient.

In a preferred embodiment of the present invention, *Osteomeles schwerinae* extract and its fractions were confirmed to be not only effective in inhibiting advanced glycation endproduct generation (Table 2, FIGS. 3-8), cross-linking with other proteins (FIGS. 9, 11, 13, 15 and 17), and aldose reductase activity (Table 6, FIGS. 18-31) but also effective in breaking cross-linking already made between advanced glycation endproduct and protein (FIGS. 12, 14, 16 and 18) and at the same time to have anti-oxidative effect as well (Table 7), suggesting that they can be effectively used for the prevention and improvement of diabetic complications.

*Osteomeles schwerinae* extract was treated to the normal group animals (SD rats) once a day for 8 weeks at the dose of 200 mg/kg/day. During the administration, no rats were dead. Blood ALT and AST levels of the animals were in the normal range, suggesting that livers of the animals were not affected by the treatment (Table 9). Therefore, the extract is evaluated as a safe substance without biotoxicity, so that it can be effectively applied to functional health food.

The functional food of the present invention can additionally include various flavors or natural carbohydrates. The natural carbohydrates above can be one of monosaccharides such as glucose and fructose, disaccharides such as maltose and sucrose, polysaccharides such as dextrin and cyclodextrin, and glucose alcohols such as xilytole, sorbitol and erythritol. Besides, natural sweetening agents such as thaumatin and stevia extract, and synthetic sweetening agents such as saccharin and aspartame can be included as a sweetening agent. The content of the natural carbohydrate is preferably 0.01~0.04 weight part and more preferably 0.02~0.03 weight part in 100 weight part of the functional health food of the present invention.

In addition to the ingredients mentioned above, the functional health food of the present invention can include a variety of nutrients, vitamins, minerals, flavors, coloring agents, pectic acid and its salts, alginic acid and its salts, organic acid, protective colloidal viscosifiers, pH regulators, stabilizers, antiseptics, glycerin, alcohols, carbonators which used to be added to soda, etc. The functional health food of the present invention can also include fruit flesh addable to natural fruit juice, fruit beverages and vegetable beverages. All the mentioned ingredients can be added singly or together. The mixing ratio of those ingredients does not matter in fact, but in general, each can be added by 0.01~0.1 weight part per 100 weight part of the functional health food of the present invention.

The present invention further provides a pharmaceutical composition or a functional health food for the prevention or postponement of aging, comprising *Osteomeles schwerinae* extract or its fractions as an active ingredient.

In a preferred embodiment of the present invention, anti-oxidative effect of *Osteomeles schwerinae* extract and its fractions was investigated. As a result, the *Osteomeles schwerinae* extract and its fractions of the present invention demonstrated as good as or better anti-oxidative effect than the conventional anti-oxidants, vitamin C, vitamin E, and BHT (butylated hydroxytoluene) (see Table 7). Therefore, the *Osteomeles schwerinae* extract and its fractions of the present invention can eliminate oxidative stress that is one of direct reasons for aging, suggesting that the extract of the present invention can be effectively used for the preparation of a pharmaceutical composition or a functional health food for the inhibition or postponement of aging.

The present invention also provides a pharmaceutical composition for the prevention and treatment of cancer or a functional health food for the prevention and improvement of cancer, comprising *Osteomeles schwerinae* extract or its fractions as an active ingredient.

The fact that advanced glycation endproduct causes cancer has already been reported (Tokuda H. et al., 2005, Book of Abstract of 53rd GA Congress joint with SIF, P076). In a preferred embodiment of the present invention, *Osteomeles schwerinae* extract or its fractions were confirmed to inhibit advanced glycation endproduct generation effectively (Table 2, FIGS. 3-18), inhibit cross-linking between advanced glycation endproduct and other proteins, and at the same time break cross-linking that has already made (FIGS. 9-18). Therefore, it was confirmed that the extract of the present invention can be effectively used for the preparation of a pharmaceutical composition or a functional health food for the prevention and treatment of cancer.

The present invention also provides a method for the treatment of diabetic complications containing the step of administering a pharmaceutically effective dose of *Osteomeles schwerinae* extract or its fractions to a subject having diabetic complications.

In a preferred embodiment of the present invention, the *Osteomeles schwerinae* extract or its fractions of the invention inhibited advanced glycation endproduct generation (see Table 2 and FIGS. 3-18), which is one of the reasons of diabetic complications, and inhibited aldose reductase activity (see Table 6), which is another reason of diabetic complications. It was also confirmed that the extract of the present invention could effectively inhibit diabetic cataract, one of diabetic complications through ex vivo (see FIGS. 19-22) and in vivo (see FIGS. 23-40) experiments. The above results indicate that the extract and its fractions of the present invention can be administered to a subject with diabetic complications to treat the complications.

The subject to which the mentioned treatment method can be applied is not only the mouse used in this invention but also other vertebrates. The applicable subject is preferably mammals and more preferably such test animals as rats, mice, rabbits, guinea pigs, hamsters, dogs and cats, and most preferably apes such as chimpanzees, gorillas and human beings.

In a preferred embodiment of the present invention, the administration is performed via external skin application and intraperitoneal injection. Since the *Osteomeles schwerinae* extract or its fractions of the present invention have no cytotoxicity, they can also be treated by oral or parenteral administration. Parenteral administration is preferably exemplified by rectal administration, intravenous injection, intramuscular injection, hypodermic injection, intrauterine injection or intracerebroventricular injection. However, external skin application is most preferred.

The effective dosage of the pharmaceutical composition of the present invention can be determined according to weight, age, gender, health condition, diet, administration frequency, administration method, excretion and severity of disease.

The present invention also provides a method for the prevention of diabetic complications containing the step of administering *Osteomeles schwerinae* extract or its fractions to a subject with diabetes.

In a subject having diabetes, blood glucose is not properly controlled, so that excessive glucose can exist in blood. When excessive glucose stays in blood for a long time, advanced glycation endproduct is generate to cause diabetic complications. At this moment, the administration of the *Osteomeles schwerinae* extract or its fractions of the present invention can inhibit advanced glycation endproduct generation in the subject, resulting in the prevention or postponement of complications of diabetic complications in the subject with diabetes.

The present invention also provides a method for the inhibition and postponement of aging containing the step of administering *Osteomeles schwerinae* extract or its fractions to a subject with diabetes.

The *Osteomeles schwerinae* extract or its fractions of the present invention have excellent anti-oxidative effect. So, the administration of the *Osteomeles schwerinae* extract or its fractions of the present invention can delay or inhibit aging in the subject with diabetes.

The present invention also provides a method for the treatment of cancer containing the step of administering *Osteomeles schwerinae* extract or its fractions to a subject with cancer, and a method for the prevention of cancer containing the step of administering *Osteomeles schwerinae* extract or its fractions to a subject.

The *Osteomeles schwerinae* extract or its fractions of the present invention can inhibit advanced glycation endproduct generation effectively, so that the administration of the *Osteomeles schwerinae* extract or its fractions of the present invention can effectively prevent and treat cancer in a subject having cancer.

The present invention relates to a functional food for the prevention or treatment of diabetic complications, the inhibition and postponement of aging, or the prevention or treatment of cancer, comprising *Osteomeles schwerinae* extract or each fraction obtained by systematic fractionation (hexane layer, ethyl acetate layer, butanol layer and water layer) as an active ingredient. The said functional food can additionally include other food ingredients with considering the marketability of the final product and customers' preference.

In addition, the present invention provides a composition complications comprising *Osteomeles schwerinae* extract or its fractions containing 2-O-acetylvitexin, hyperoside and quercitrin as an active ingredient.

The compounds such as betulinic acid-3β-yl-caffeate, betuline-3β-yl-caffeate, 2-O-acetylvitexin, quercitrin, hyperoside, afzelin, and (−)-epicatechin have been isolated from *Osteomeles schwerinae* extract. Each of those compounds was also confirmed to inhibit advanced glycation endproduct generation and aldose reductase activity (see Tables 2 and 6). Therefore, *Osteomeles schwerinae* extract or its fractions containing the said compounds can be used as a composition for the prevention and treatment of diabetic complications.

Practical and presently preferred embodiments of the present invention are illustrative as shown in the following Examples, Experimental Examples and Manufacturing Examples.

However, it will be appreciated that those skilled in the art, on consideration of this disclosure, may make modifications and improvements within the spirit and scope of the present invention.

Example 1

Preparation of Ethanol Extract of *Osteomeles schwerinae* Small Twigs and Leaves

*Osteomeles schwerinae* (Rosaceae) used in this invention was obtained in Yunnan, China, and the evidence sample (no. KIOM-OS) has been stored at Plant Specimen Lab in Diabetic Complication Research Center at Oriental Medical Technology Research Center of Korea Institute of Oriental Medicine. Small twigs, leaves, and seeds of *Osteomeles schwerinae* were dried in the shadow and chopped, which were placed in an extraction vessel containing ethanol. Extraction was performed at room temperature 2~5 times. Ethanol extract was obtained by concentrating the extract under reduced pressure at 40° C. To prevent degradation and hydrolysis of each component, the temperature for the concentration was preferably maintained lower than 40-45° C. In this invention, 120 g of dried/chopped *Osteomeles schwerinae* was added in 1 l of ethanol, followed by extraction at room temperature three times. The extract was concentrated under reduced pressure at 40° C. As a result, 12 g of ethanol extract was obtained.

Example 2

Preparation of Hexane Fraction of *Osteomeles schwerinae* Twig/Leaf Extract

Hexane layer was separated after mixing 12 g of the ethanol extract obtained in Example 1, 0.5 l of water and 0.5 l of normal hexane. This process was repeated three times, followed by concentration under reduced pressure at 40° C. As a result, 1.28 g of hexane fraction was obtained.

Example 3

Preparation of Ethyl Acetate Fraction of *Osteomeles schwerinae* Twig/Leaf Extract Water layer was separated after mixing 12 g of the ethanol extract obtained in Example 1, 0.5 l of water and 0.5 l of normal hexane. Ethyl acetate layer was separated after mixing the water layer and 0.5 l of ethyl acetate. This process was repeated three times, followed by concentration under reduced pressure at 40° C. As a result, 3.75 g of ethyl acetate fraction was obtained.

Example 4

Preparation of Normal Butanol Fraction of *Osteomeles schwerinae* Twig/Leaf Extract After adding 0.5 l of water and 0.5 l of normal hexane to the ethanol extract obtained in Example 1, hexane layer was eliminated and ethyl acetate was added to water layer. Water layer was obtained by eliminating ethyl acetate layer. Normal butanol layer was obtained after mixing the water layer and 0.5 l of normal butanol. This process was repeated three times, followed by concentration under reduced pressure at 40° C. As a result, 4.10 g of butanol fraction was obtained.

Example 5

Preparation of Water Fraction of *Osteomeles schwerinae* Twig/Leaf Extract

After adding 0.5 l of water and 0.5 l of normal hexane to 12 g of the ethanol extract obtained in Example 1, hexane layer was eliminated and ethyl acetate was added to water layer. After eliminating ethyl acetate layer, normal butanol was added thereto. After eliminating normal butanol layer, concentration was performed under reduced pressure at 40° C. As a result, 2.87 g of water fraction was obtained.

Example 6

Preparation of *Osteomeles schwerinae* Seed Extract

*Osteomeles schwerinae* seed extract was prepared by the same manner as described in Example 1 except that seeds of *Osteomeles schwerinae* were used instead of small twigs and leaves of *Osteomeles schwerinae*.

Example 7

Standardization of *Osteomeles schwerinae* Extract

Extraction solvents used in this invention were all extra pure solvents (Daejung Chemical & Metals Co., LTD, Korea). Moving phase solvent methanol (Fisher Scientific, USA) and water (J.T.Backer, USA) used for HPLC were all HPLC-grade. 1200 analytical HPLC system (Agilent) was used for HPLC herein, which was composed of binary pump (G1312A), vacuum degasser (G1322A), thermostatted column compartment (G1316A), multiple wavelength detector (1365B, MWD), and autosampler (G1329A). ChemStation software was used for the operation of devices and the treatment of analysis results. Spherex C-18 column (4.6 mm×250, i.d., 5.0 m, Phenomenex) was used for analysis. Four kg of *Osteomeles schwerinae* dried at room temperature was pulverized, followed by extraction with 99% ethanol at room temperature for 24 hours three times. After filtering and concentrating, 104.16 kg of ethanol extract was obtained. The ethanol extract was prepared at the concentration of 4 mg/ml. HPLC was performed after injecting 10 μl of the prepared ethanol extract into column. Standard 2"-O-acetylvitexin was dissolved in 100% methanol, followed by two-fold dilution to prepare standard solutions for calibration curve at the concentrations of 100, 50, 25, 10, and 5 μg/ml. Standard hyperoside and quercitrin were dissolved in 100% methanol, followed by two-fold dilution to prepare standard solutions for calibration curve at the concentrations of 100, 50, 25, 12.5, and 6.25 μg/ml. Each standard solution for calibration curve was loaded in column, followed by HPLC to obtain chromatogram. Each calibration curve for quantitative analysis was prepared by plotting the peak data. Spherex C-18 column (4.6 mm×250, i.d., 5.0 m, Phenomenex) was used for HPLC. Column temperature was set at 30° C. and wavelength of UV detector was set at 254 nm. Each sample was loaded by using the autosampler by 10 μl. Moving phase was the mixed solution of 0.1% acetic acid and methanol. Flow velocity was set at 1.0 ml/min. Composition gradient of the moving phase was as follows: 25~45% methanol (0~40 min.)→45~70% methanol (40~55 min.)→70~100% methanol (55~65 min.)→100% methanol (65~70 min.).

Figure 2:
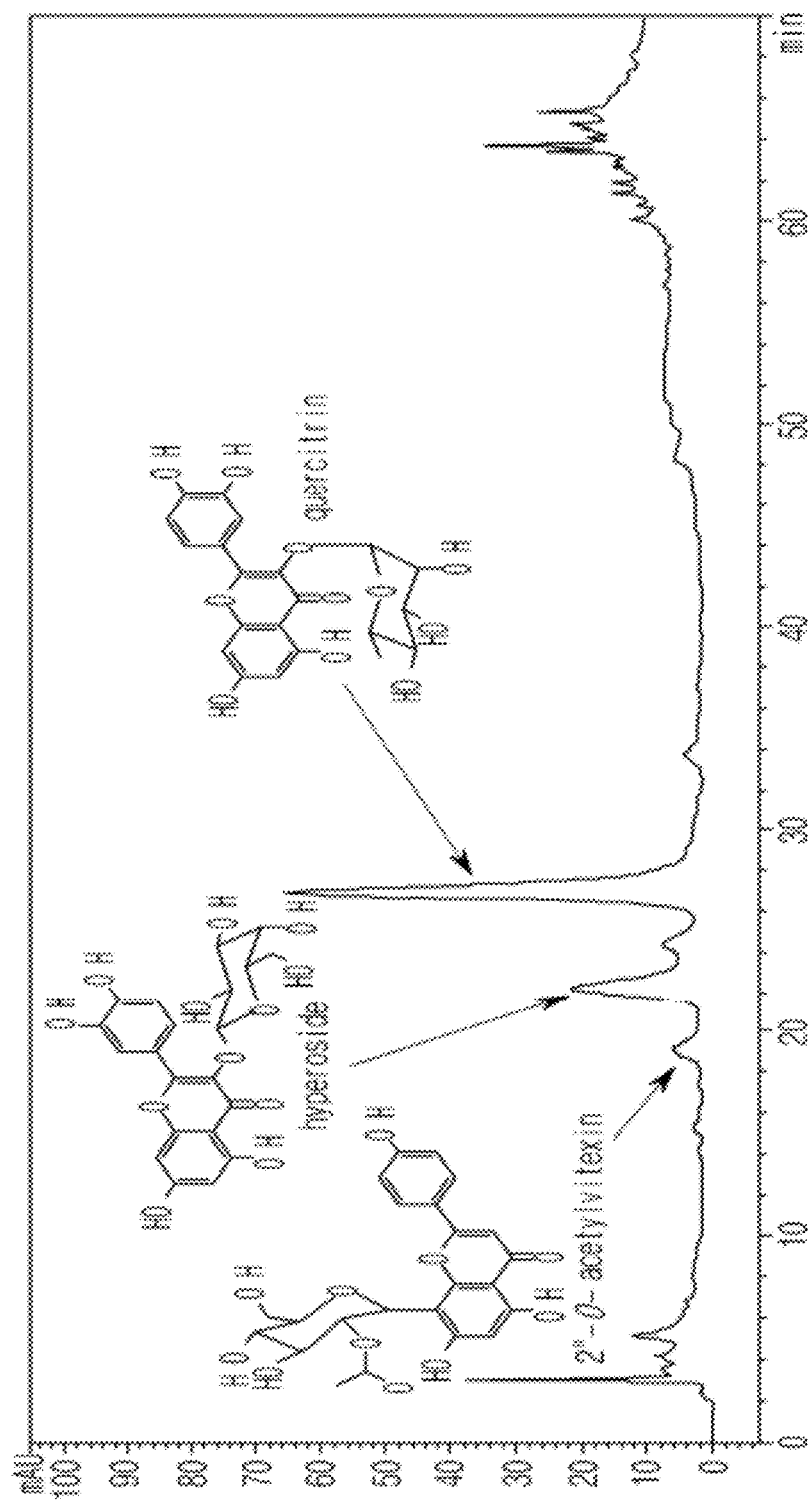
FIG. 2 is HPLC chromatogram of *Osteomeles schwerinae* extract.

The results of HPLC analyzing *Osteomeles schwerinae* extract are shown in FIG. 2 and in Table 1. As seen, three kinds of flavonoid compounds, which are quercitrin, hyperoside, and 2"-O-acetylvitexin, were confirmed on HPLC chromatogram as three major components (FIG. 2). Thus, contents of the three kinds of major components of *Osteomeles schwerinae* extract were simultaneously analyzed by HPLC. As a result, it was confirmed that the contents of quercitrin, hyperoside, and 2"-O-acetylvitexin were respectively 3.44%, 1.58%, and 0.54% (Table 1).

TABLE 1

| compounds | content (mean ± SD n = 3) | |
|---|---|---|
| | mg/g | (%) |
| 2-O-acetylvitexin | 5.40 ± 0.38 | 0.54 |
| hyperoside | 15.78 ± 0.62 | 1.58 |
| quercitrin | 34.43 ± 0.96 | 3.44 |

Table 1 shows contents of the major components of *Osteomeles schwerinae* extract.

Experimental Example 1

Analysis of Inhibitory Effect on Advanced Glycation Endproduct Generation

<1-1> In Vitro Analysis of Inhibitory Effect on Advanced Glycation Endproduct Generation Inhibitory effect of *Osteomeles schwerinae* small twig/leaf extract, fractions thereof obtained from each of hexane layer, ethyl acetate layer, butanol layer and water layer of the extract, and *Osteomeles schwerinae* seed extract on advanced glycation endproduct generation was investigated in vitro. Bovine serum albumin (BSA, Sigma, USA) was used as a protein source. BSA was added to 50 mM phosphate buffer (pH 7.4) at the concentration of 10 mg/ml. As a sugar source, the mixed solution of 0.2 M fructose and 0.2 M glucose was used. The mixed solution of fructose and glucose was added to the BSA solution. *Osteomeles schwerinae* small twig/leaf extract was prepared at different concentrations of 5 μg/ml, 10 μg/ml and 25 μg/ml. Hexane layer was also prepared at the concentrations of 10 μg/ml, 25 μg/ml and 50 μg/ml. Ethyl acetate layer was prepared at different concentrations of 5 μg/ml, 10 μg/ml and 25 μg/ml. Butanol layer and water layer were respectively prepared at the concentrations of 2.5 μg/ml, 5 μg/ml and 10 μg/ml. *Osteomeles schwerinae* seed extract was also prepared at different concentrations of 5 μg/ml, 10 μg/ml and 25 μg/ml. (All of those compounds were dissolved in DMSO, to which 15% tween 80 was added. At this time, the content of DMSO was 0.2%). Each extract or fraction was mixed with the mixed solution of BSA and sugars, followed by culture at 37° C. for 14 or 28 days. At this time, 0.02% sodium azide and antimycotics were added thereto as the antibacterial and antifungal agent. For the control, the mixed solution of BSA and sugars was cultured. The blank groups of each experimental and the control were composed as the above but not cultured. For the positive control, which would be used as an index for the comparison of the effect, aminoguanidine was used. To avoid error, 4 of each culture solution were prepared. 14 or 28 days later, the content of advanced glycation endproducts generated in each culture solution was measured and compared. AGEs therein were fluorescent and brown colored. They have physiochemical properties for the cross-linking and also have ligand that can be recognized by cell membrane receptor. The amount of AGEs having the said properties was measured with microplate reader (Excitation: 350 nm, Emission: 450 nm) to analyze the inhibitory effect on the generation of AGEs (Vinson, J. A. et al., *J. Nutr. Biochem.*, 7: 659-663, 1996).

Inhibitory rate of generation was calculated by the following formula.

Inhibitory rate of generation(%)=100−(fluorescence intensity of experimental group sample−fluorescence intensity of empty sample)/(fluorescence intensity of control group sample−fluorescence intensity of control group empty sample)×100

Positive Control: Analysis of Inhibitory Effect of Aminoguanidine on Advanced Glycation Endproduct Generation Aminoguanidine was dissolved in distilled water and then cultured at the concentrations of 37 μg/ml, 55.5 μg/ml and 74 μg/ml at 37° C. for 14 days and also cultured at the concentrations of 18.5 μg/ml, 37.0 μg/ml and 92.5 μg/ml for 28 days by the same manner as described above. The amount of advanced glycation endproducts generated in each culture solution was measured with microplate reader (Excitation: 350 nm, Emission: 450 nm). Inhibitory effect of *Osteomeles schwerinae* small twig/leaf extract, its fractions and *Osteomeles schwerinae* seed extract on advanced glycation endproduct generation was measured in vitro by the same manner as described above and the results are shown in Table 2.

TABLE 2

| Compound/ effect | Concentration (μg/ml) | | Inhibitory effect (%) | | inhibitory effect ($IC_{50}$, μg/ml) | |
|---|---|---|---|---|---|---|
| | 14 day | 28 day | 14 day | 28 day | 14 day | 28 day |
| extract of *Osteomeles schwerinae* small twigs and leaves | 5<br>10<br>25 | 5<br>10<br>25 | 3.96 ± 0.58<br>37.44 ± 0.25<br>77.51 ± 0.34 | 2.23 ± 0.30<br>24.30 ± 0.20<br>76.94 ± 0.27 | 16.34 | 17.64 |
| hexane fraction of *Osteomeles schwerinae* twig/leaf extract | 10<br>25<br>50 | 50 | −0.45 ± 1.36<br>17.00 ± 1.49<br>68.35 ± 3.01 | 33.84 ± 0.32 | 40.71 | >50 |
| ethyl acetate fraction of *Osteomeles schwerinae* twig/leaf extract | 5<br>10<br>25 | 5<br>10<br>25 | −0.87 ± 0.90<br>26.45 ± 0.13<br>83.82 ± 0.33 | 5.89 ± 0.43<br>17.91 ± 0.15<br>75.41 ± 0.20 | 16.61 | 18.09 |
| butanol fraction of *Osteomeles schwerinae* twig/leaf extract | 2.5<br>5<br>10 | 5<br>10<br>25 | 2.71 ± 0.79<br>18.38 ± 1.48<br>66.94 ± 1.24 | 5.36 ± 0.20<br>29.74 ± 0.39<br>87.13 ± 0.33 | 8.20 | 15.63 |
| water fraction of *Osteomeles schwerinae* twig/leaf extract | 2.5<br>5<br>10 | 5<br>10<br>25 | −4.51 ± 1.17<br>12.17 ± 0.76<br>68.27 ± 0.58 | 5.14 ± 0.46<br>32.42 ± 0.25<br>85.59 ± 0.07 | 8.32 | 15.62 |
| *Osteomeles schwerinae* seed extract | 5<br>10<br>25 | 5<br>10<br>25 | 18.20 ± 0.87<br>41.14 ± 0.85<br>85.69 ± 0.72 | 0.51 ± 0.95<br>10.02 ± 0.84<br>90.13 ± 0.58 | 13.93 | 20.20 |
| Amino-guanidine | 37<br>55.5<br>74 | 18.5<br>37.0<br>92.5 | 27.42 ± 1.51<br>39.96 ± 0.90<br>51.77 ± 1.91 | 14.89 ± 4.11<br>24.93 ± 3.46<br>50.41 ± 0.41 | 71.13 | 91.30 |

As shown in Table 2, the inhibitory effect of *Osteomeles schwerinae* small twig/leaf extract and seed extract on advanced glycation endproduct generation was presented as $IC_{50}$ value as follows: 16.34 μg/ml (small twig/leaf extract, 14 days), 17.64 μg/ml (small twig/leaf extract, 28 days), 13.93 μg/ml (seed extract, 14 days), and 20.20 μg/ml (seed extract, 28 days), which were 4 times or 5 times higher than that of the positive control, amino-guanidine ($IC_{50}$: 71.13 μg/ml, 91.30 μg/ml). Inhibitory effect of fractions of *Osteomeles schwerinae* small twig/leaf extract on advanced glycation endproduct generation was also measured and as a result butanol layer showed the most excellent inhibitory effect, followed by water layer, ethyl acetate layer, and hexane layer in that order. Compared with the positive control, all the fractions demonstrated higher inhibitory effect (see Table 2). That is, *Osteomeles schwerinae* extract and its fractions inhibited the generation of advanced glycation endproducts by suppressing protein-sugar binding.

<1-2> Analysis of AGEs-BSA Content by ELISA

Figure 3:
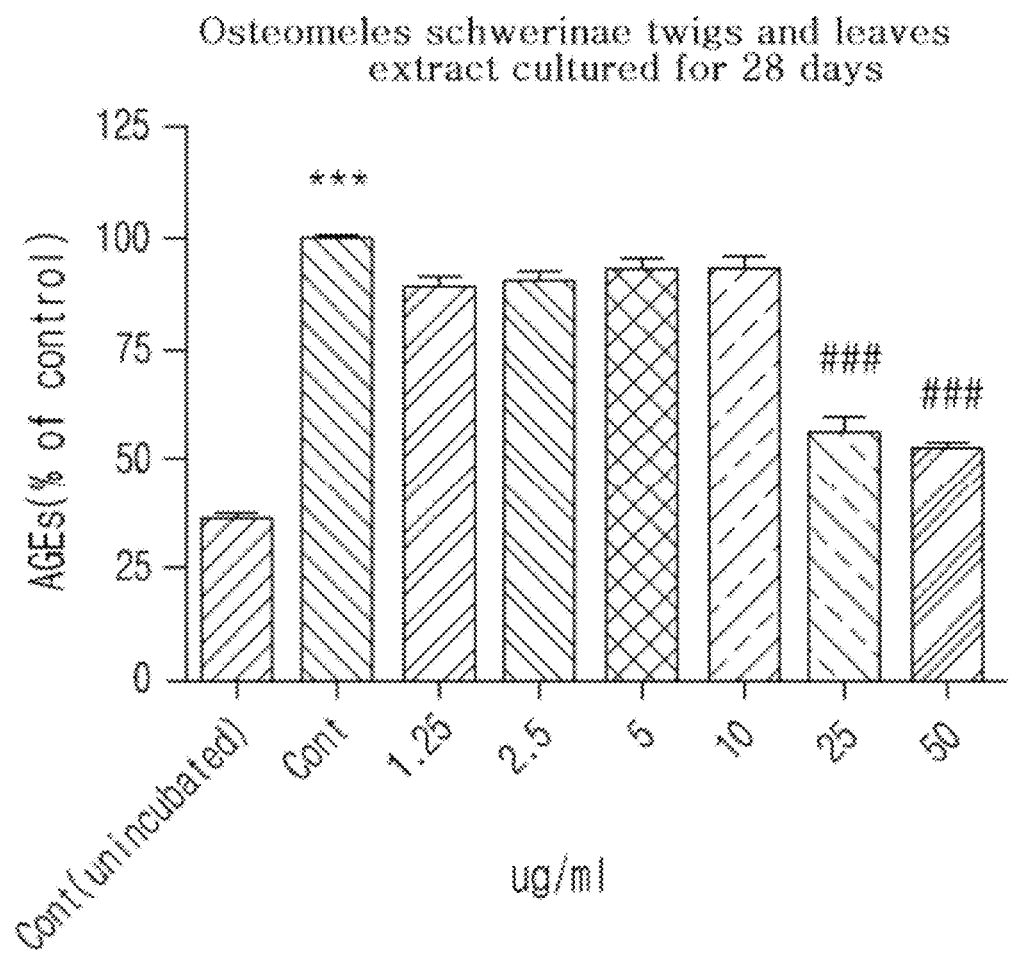
FIG. 3 is a graph illustrating the AGE-BSA content in the *Osteomeles schwerinae* extract cultured for 28 days, which was analyzed by ELISA.
Figure 4:
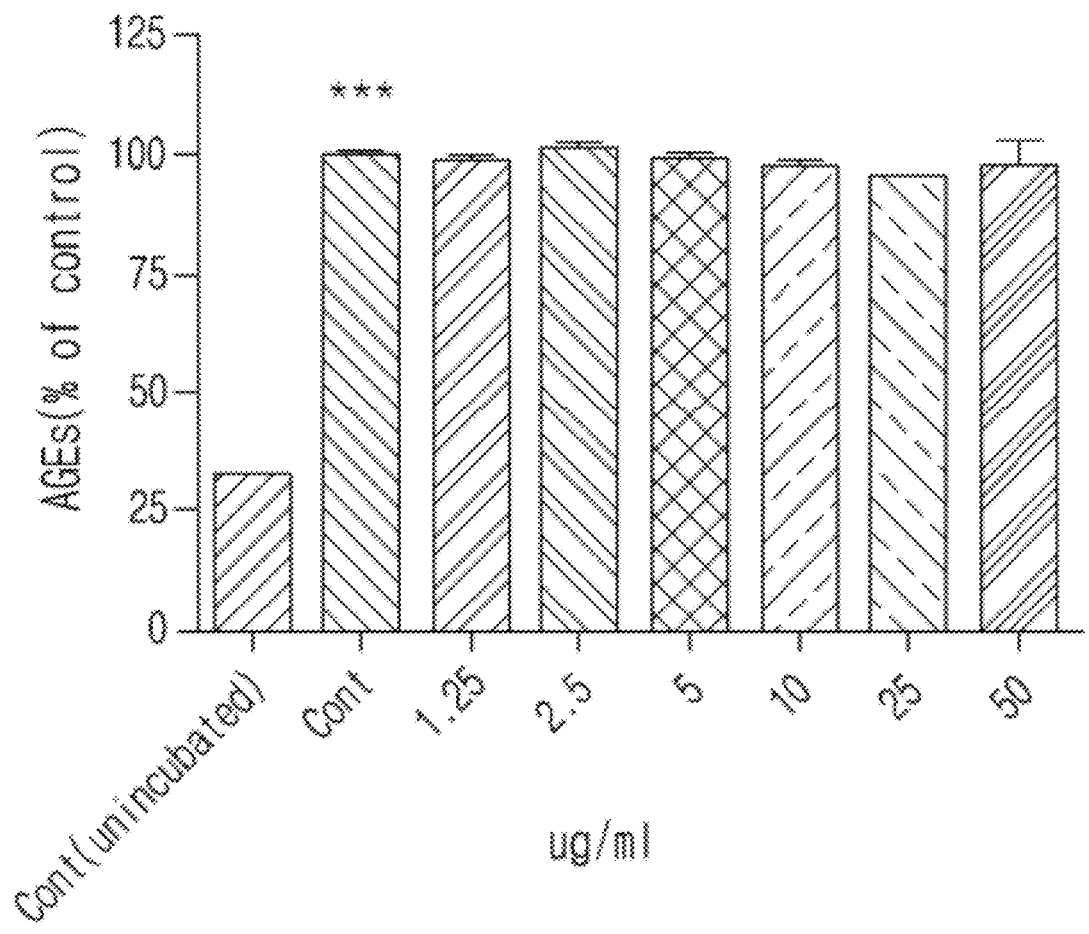
FIG. 4 is a graph illustrating the AGE-BSA content in hexane layer of the *Osteomeles schwerinae* extract cultured for 28 days, which was analyzed by ELISA.

Since it was proved that the extract and its fractions of the present invention had excellent inhibitory effect on advanced glycation endproduct generation, ELISA, an immunological assay method, was performed by using AGEs-specific antibody to reconfirm the effect. AGEs-ELISA was performed by Engvall's method (Engvall, E., et al., *J immunochem.*, 1971, 8:871-874). Samples were mixed with coating buffer (50 mM carbonate buffer, pH 9.6) at the ratio of 1:2, and load in a 96 well plate (100 μl/well), which stood at 37° C. for 2 hours. After washing with 0.05% PBST three times, blocking was performed with 1% BSA/PBS. The plate stood for 1 hour and then washed again with 0.05% PBST three times. AGE antibody (6D12, TransGenic Inc., Kobe, Japan) was diluted at the ratio of 1:1000, which was loaded in the well plate (100 μl/well), which stood at room temperature for 1 hour. Then, the plate was washed with 0.05% PBST three times. HRP-conjugate $2^{nd}$ antibody (Santa Cruz, USA) was diluted at the ratio of 1:1000, which was loaded in the well plate (100 μl/well), which stood for 1 hour. The plate was then washed with 0.05% PBST three times, to which 100 μl of substrate 3,3',5,5'-Tetramethylbenzidine (TMB) was added. 5 minutes later, reaction termination solution (1M $H_2SO_4$) was added thereto (100 μl/well). OD was measured with ELISA reader. As a result, the inhibitory effect of *Osteomeles schwerinae* small twig/leaf extract and its fractions on AGEs generation was confirmed as follows (see Table 3). As shown in FIG. 3, it was confirmed from the analysis of AGE-BSA content by ELISA that *Osteomeles schwerinae* small twig/leaf extract cultured for 28 days showed significant inhibitory effect on AGEs generation at the concentrations of 25 and 50 μg/ml (### $p<0.001$ vs. Control). From the analysis of AGE-BSA content by ELISA, it was confirmed that hexane layer of *Osteomeles schwerinae* small twig/leaf extract cultured for 28 days did not show inhibitory effect on AGEs generation. As shown in Table 1, $IC_{50}$ value was 50 μg/ml (see FIG. 4).

Figure 5:
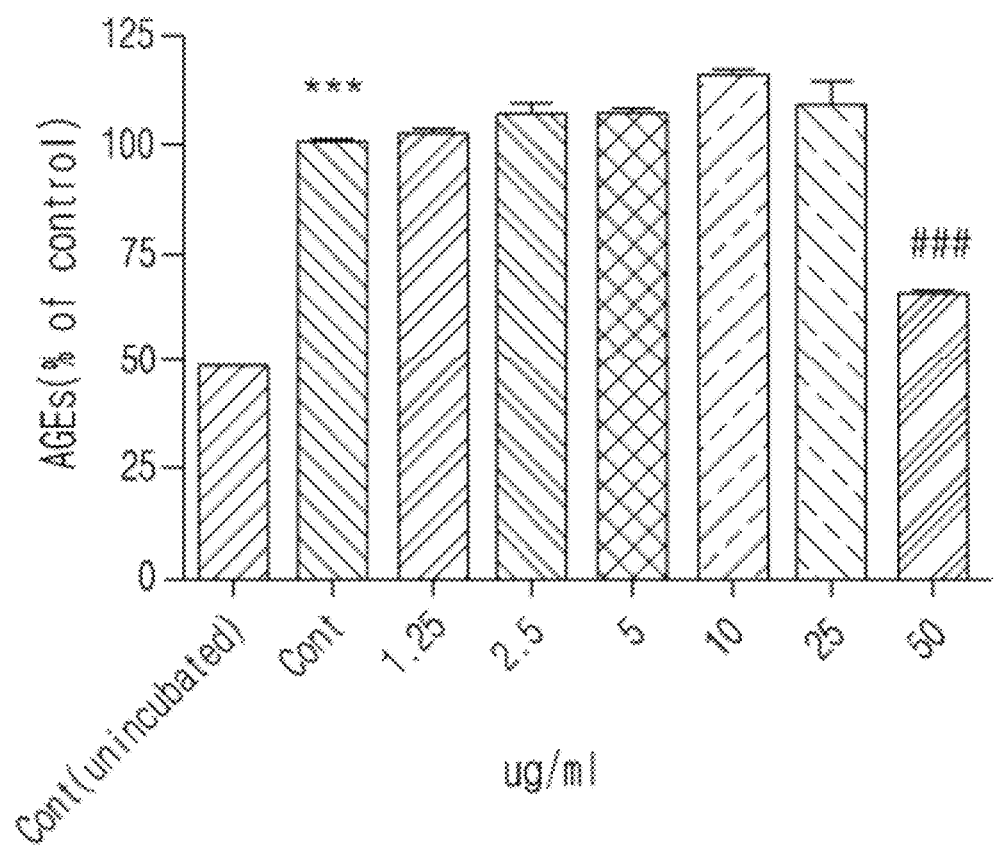
FIG. 5 is a graph illustrating the AGE-BSA content in ethyl acetate layer of the *Osteomeles schwerinae* extract cultured for 28 days, which was analyzed by ELISA.
Figure 6:
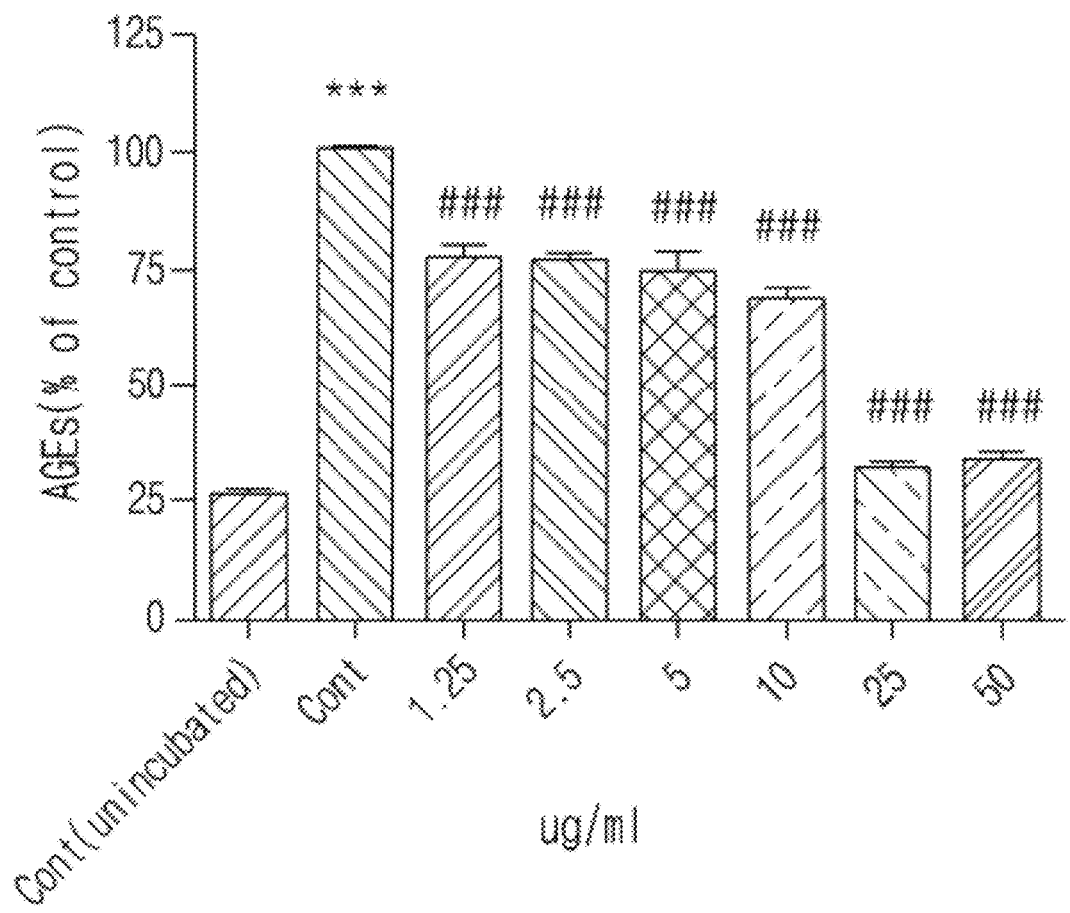
FIG. 6 is a graph illustrating the AGE-BSA content in butanol layer of the *Osteomeles schwerinae* extract cultured for 28 days, which was analyzed by ELISA.
Figure 7:
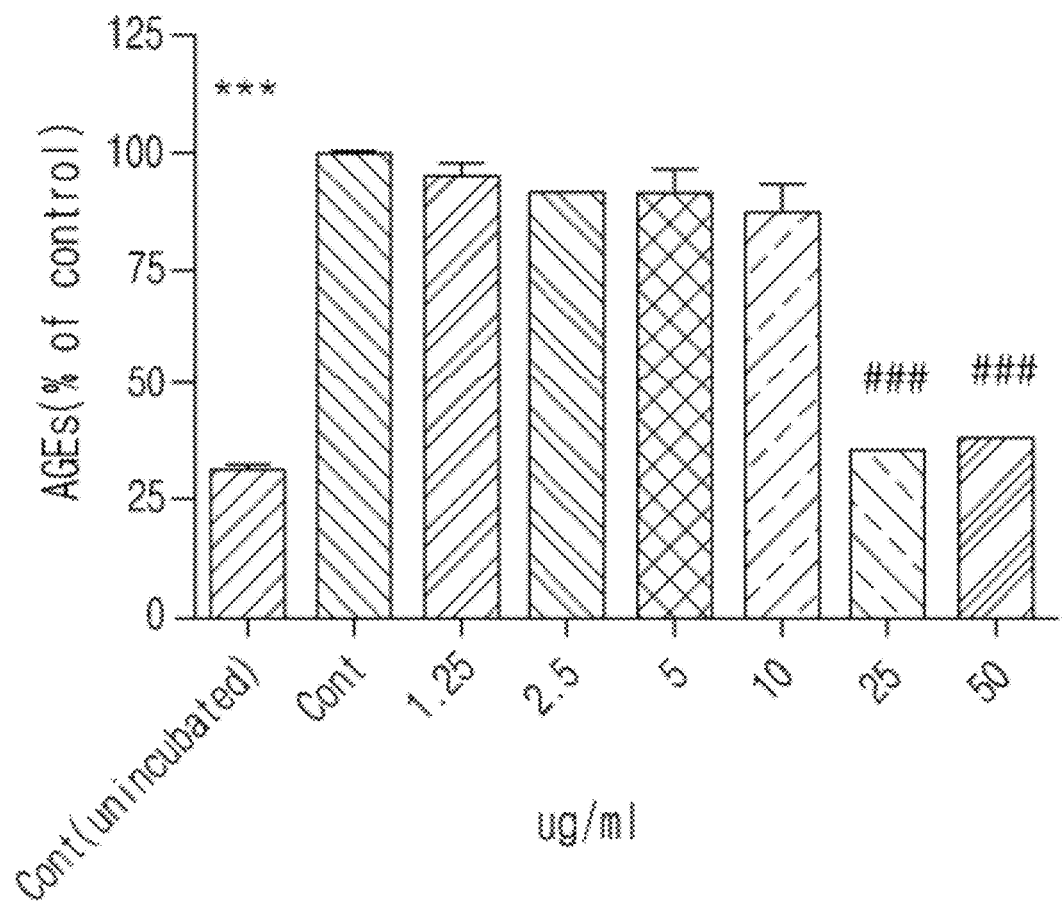
FIG. 7 is a graph illustrating the AGE-BSA content in water layer of the *Osteomeles schwerinae* extract cultured for 28 days, which was analyzed by ELISA.

It was also confirmed from the analysis of AGE-BSA content by ELISA that ethyl acetate layer of *Osteomeles schwerinae* small twig/leaf extract cultured for 28 days showed significant inhibitory effect on AGEs generation at the concentration of 50 μg/ml (see FIG. 5). From the analysis of AGE-BSA content by ELISA, it was confirmed that butanol layer of *Osteomeles schwerinae* small twig/leaf extract cultured for 28 days showed significant inhibitory effect on AGEs generation at the concentrations of 1.25, 2.5, 5.0, 10, 25 and 50 μg/ml (see FIG. 6). From the analysis of AGE-BSA content by ELISA, it was confirmed that water layer of *Osteomeles schwerinae* small twig/leaf extract cultured for 28 days showed significant inhibitory effect on AGEs generation at the concentrations of 25 and 50 μg/ml (see FIG. 7).

Figure 8:
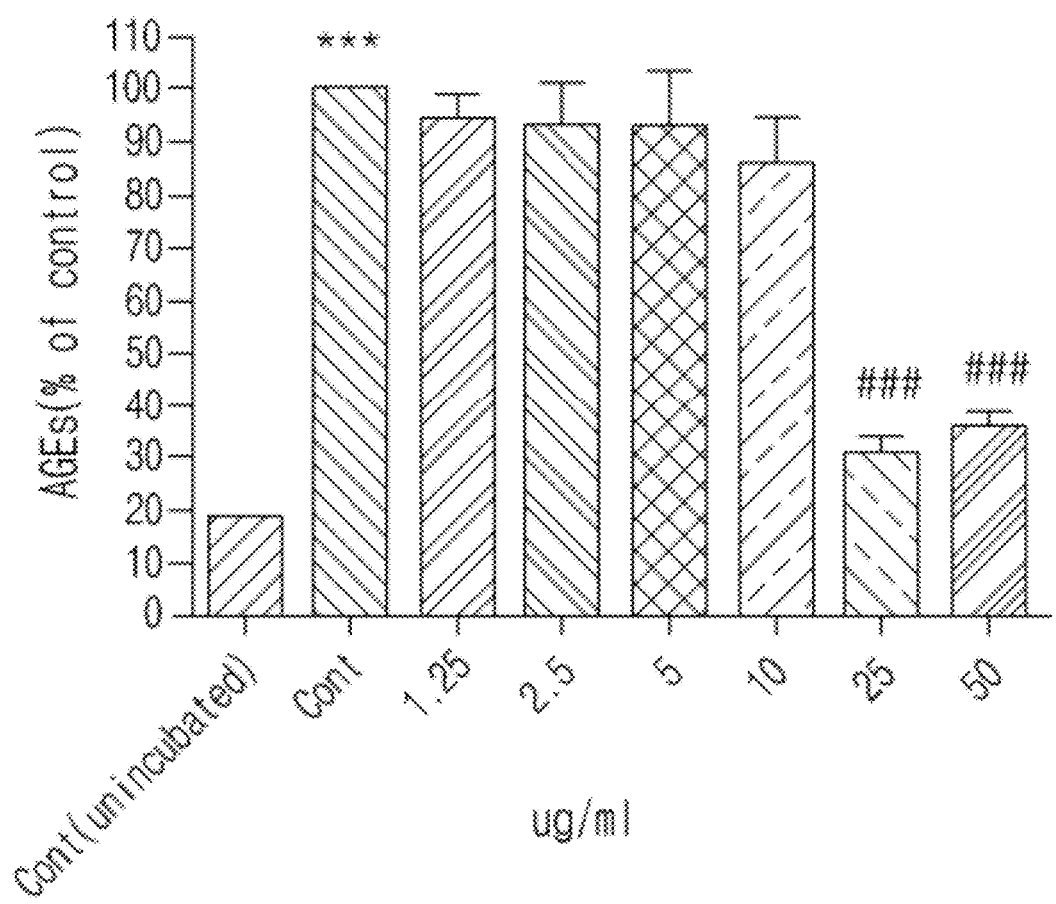
FIG. 8 is a graph illustrating the AGE-BSA content in the *Osteomeles schwerinae* seed extract cultured for 28 days, which was analyzed by ELISA.

In the experiments using *Osteomeles schwerinae* seed extract, the following result was obtained. From the analysis of AGE-BSA content by ELISA, it was confirmed that *Osteomeles schwerinae* seed extract cultured for 28 days showed significant inhibitory effect on AGEs generation at the concentrations of 25 and 50 μg/ml (see FIG. 8). As shown in FIG. 8, the results of AGEs-BSA content analysis using ELISA were consistent with those of in vitro AGEs generation inhibition test.

<1-3> Examination of Inhibition or Breaking Effect on Advanced Glycation End Products (AGEs) Cross-Link It was investigated if the extract of the present invention had inhibitory effect on cross-link between advanced glycation endproducts and proteins to generate glycoproteins, or if the extract of the present invention had breaking effect on the cross-link between advanced glycation endproducts and proteins, or if the extract had both inhibitory and breaking effect on the cross-link.

1. In Vitro Assay to Evaluate Inhibitory Effect on AGEs Cross-Link 1.0 μg of AGE-BSA (MBL international, Woburn, Mass.) was mixed with samples at different concentrations and AGEs

TABLE 3

| | Cont | | Conc (μg/ml) | | |
|---|---|---|---|---|---|
| | (unincubated) | Cont | 1.25 | 2.5 | 5 |
| Example 1 (FIG. 3) | 36.13 ± 2.44 | 100.00 ± 0.00 | 89.27 ± 3.73 | 90.70 ± 4.22 | 93.47 ± 4.83 |
| Example 2 (FIG. 4) | 32.70 ± 0.30 | 100.00 ± 0.00 | 99.27 ± 1.79 | 101.77 ± 2.77 | 99.83 ± 2.75 |
| Example 3 (FIG. 5) | 48.10 ± 0.90 | 100.00 ± 0.00 | 102.43 ± 1.72 | 107.33 ± 3.93 | 107.17 ± 2.81 |
| Example 4 (FIG. 6) | 27.13 ± 1.29 | 100.00 ± 0.00 | 77.60 ± 4.26 | 76.83 ± 2.32 | 74.37 ± 8.25 |
| Example 5 (FIG. 7) | 31.97 ± 2.44 | 100.00 ± 0.00 | 95.97 ± 4.88 | 92.20 ± 1.39 | 91.77 ± 10.14 |
| Example 6 (FIG. 7) | 18.70 ± 0.69 | 100.00 ± 0.00 | 94.53 ± 8.03 | 93.33 ± 12.45 | 93.40 ± 16.80 |

| | Conc (μg/ml) | | | |
|---|---|---|---|---|
| | 10 | 2.5 | 50 | $IC_{50}$ |
| Example 1 (FIG. 3) | 94.23 ± 4.30 | 56.77 ± 6.31 | 52.97 ± 2.21 | 47.38 ± 2.69 |
| Example 2 (FIG. 4) | 98.10 ± 2.69 | 95.60 ± 1.10 | 97.33 ± 10.08 | |
| Example 3 (FIG. 5) | 116.20 ± 1.49 | 109.33 ± 10.34 | 65.93 ± 1.21 | 64.42 ± 2.19 |
| Example 4 (FIG. 6) | 68.57 ± 4.76 | 32.50 ± 2.09 | 34.43 ± 2.48 | 21.77 ± 4.35 |
| Example 5 (FIG. 7) | 88.43 ± 10.40 | 37.20 ± 1.04 | 39.80 ± 0.70 | 32.78 ± 2.02 |
| Example 6 (FIG. 7) | 86.50 ± 13.79 | 31.00 ± 4.20 | 35.43 ± 5.27 | 19.28 ± 2.25 | cross-linking inhibitor, aminoguanidine. The mixture was distributed in collagen-coated 96 well microtiter plate, followed by culture at 37° C. for 4 hours. The plate was washed with 0.05% Tween in PBS three times to eliminate unattached AGE-BSA. Rabbit polyclonal anti-AGE-BSA antibody was diluted at the ratio of 1:250, which was distributed in each well, followed by culture at 37° C. for 1 hour. One hour later, the plate was washed with 0.05% Tween in PBS three times, to which horseradish peroxidase-linked goat anti-rabbit antibody was applied. Color development was induced by using TMB as a substrate and then $OD_{450}$ was measured. Cross-linking % of AGE-BSA was calculated by the following formula.

$$AGE\text{-}BSA(\%) = (OD \text{ of the well treated with sample}/OD \text{ of the well not-treated with sample}) \times 100$$

2. In Vitro Assay to Evaluate Breaking Effect on AGEs Cross-Link 1.0 μg of AGE-BSA was distributed in collagen-coated 96 well microtiter plate, followed by culture at 37° C. for 4 hours. The plate was washed with 0.05% Tween in PBS three times to eliminate unattached AGE-BSA. Samples and ALT-711 (4,5-dimethyl-3-(2-oxo-2-phenylethyl)-thiazolium chloride; Alteon Inc., Ramsey, N.J.) known as the AGEs cross-linking breaker were two-fold diluted from the concentration of 1000 μg/l to 1 μg/l, following by loading in each well of the plate. The plate was cultured at 37° C. for 4 hours. Then, each well of the plate was washed with 0.05% Tween in PBS three times. Rabbit polyclonal anti-AGE-BSA antibody (MBL international, Woburn, Mass.) was diluted at the ratio of 1:250, which was distributed in each well, followed by culture at 37° C. for 1 hour to detect remaining AGE-BSA which was cross-linked with collagen. One hour later, the plate was washed with 0.05% Tween in PBS three times, to which horseradish peroxidase-linked goat anti-rabbit antibody (Sigma, USA) was applied. Color development was induced by using TMB (3,3',5,5'-tetramethylbenzidine) as a substrate and then $OD_{450}$ was measured. AGE-BSA breaking % was calculated by the same formula used above.

Figure 9:
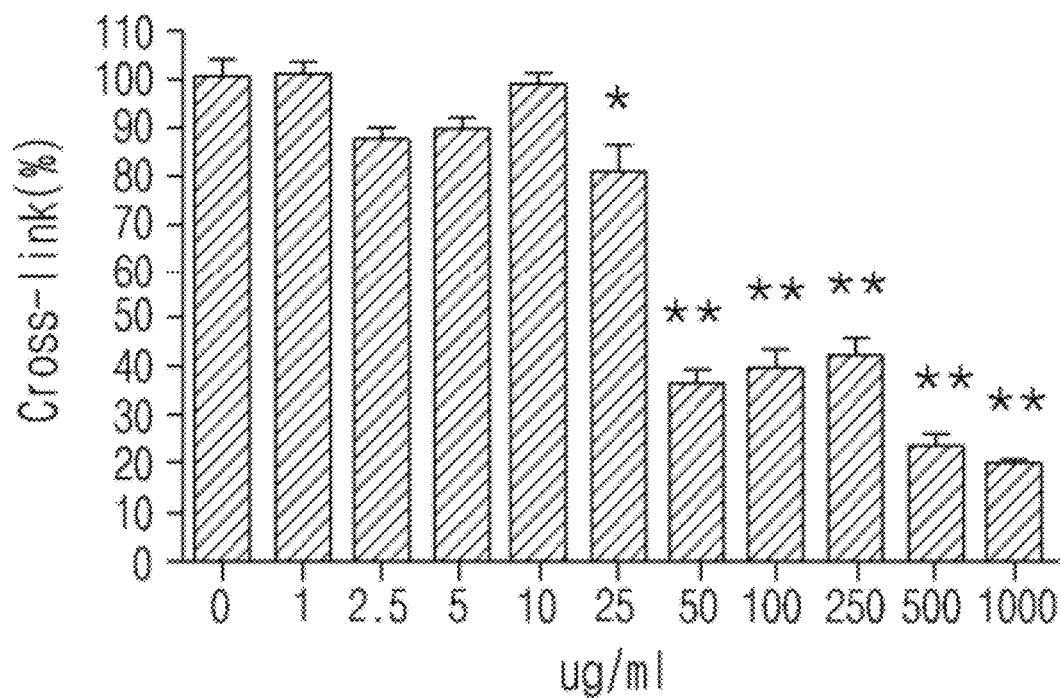
FIG. 9 is a graph illustrating the AGE-BSA inhibition effect of *Osteomeles schwerinae* extract.
Figure 10:
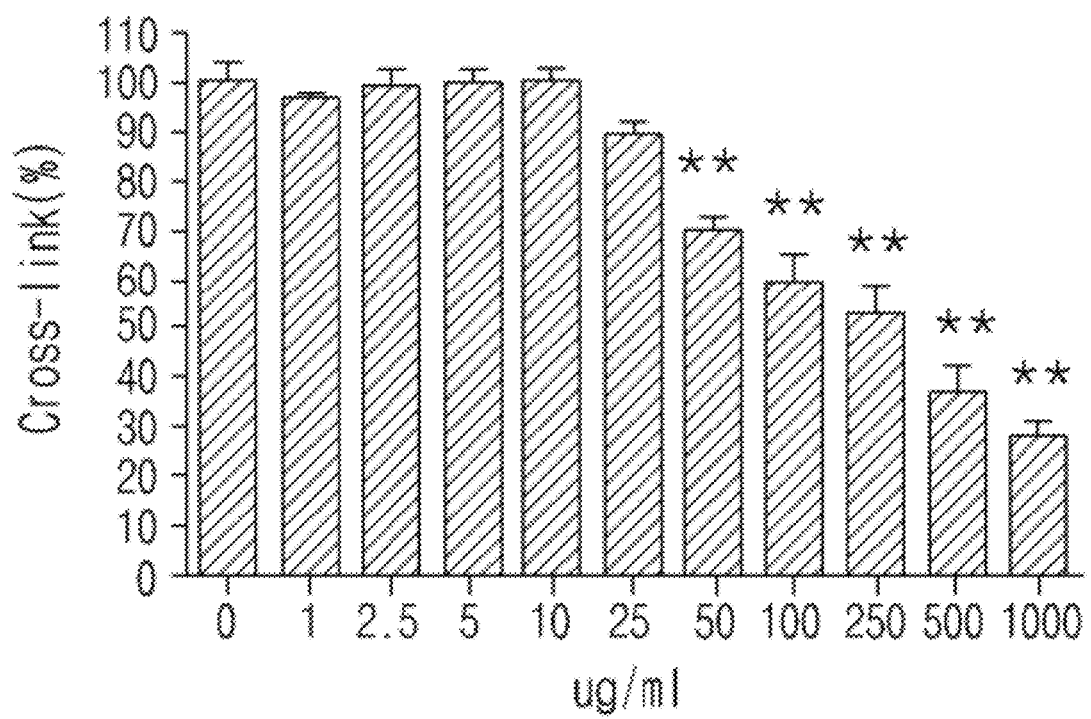
FIG. 10 is a graph illustrating the AGE-BSA breaking effect of *Osteomeles schwerinae* extract.
Figure 11:
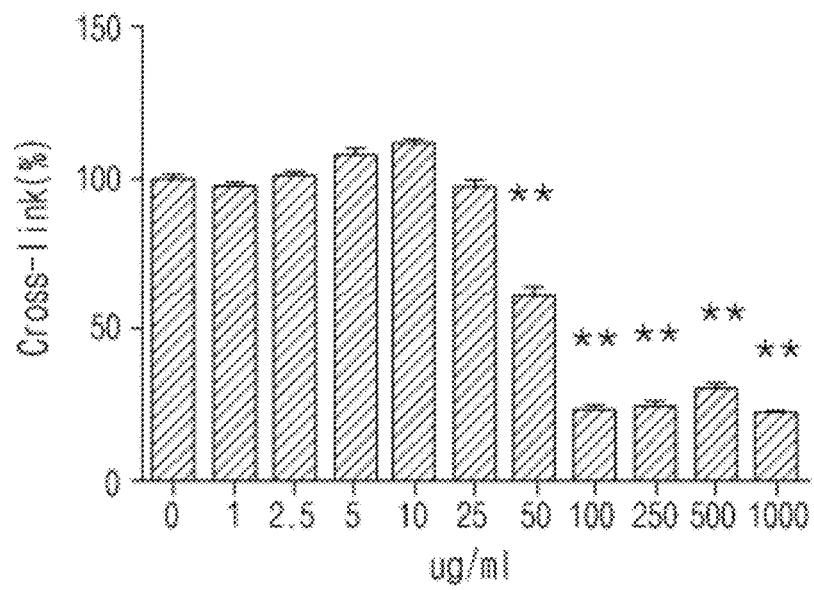
FIG. 11 is a graph illustrating the AGE-BSA inhibition effect of hexane layer of *Osteomeles schwerinae* extract.
Figure 12:
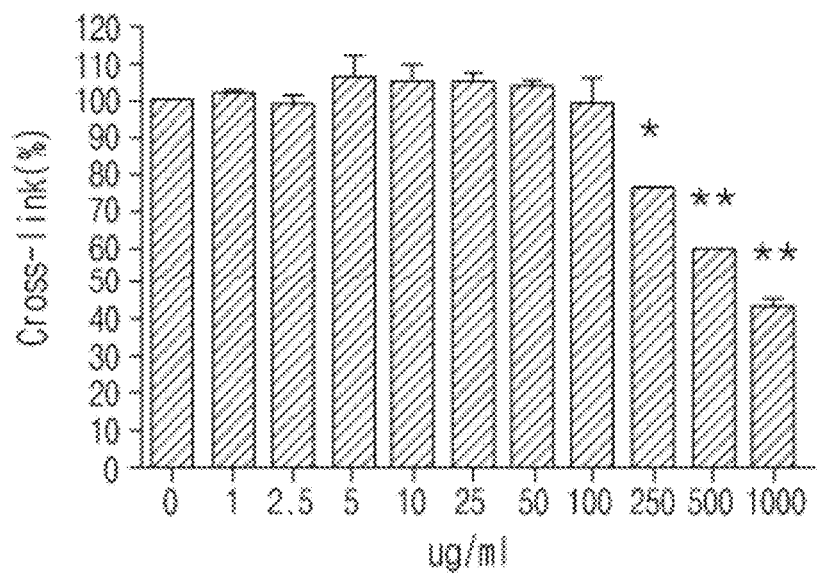
FIG. 12 is a graph illustrating the AGE-BSA breaking effect of hexane layer of *Osteomeles schwerinae* extract.
Figure 13:
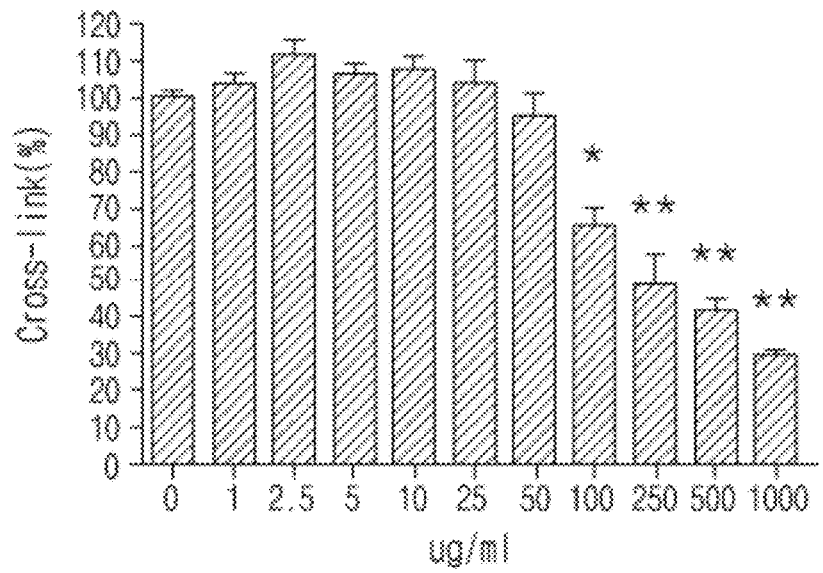
FIG. 13 is a graph illustrating the AGE-BSA inhibition effect of ethyl acetate layer of *Osteomeles schwerinae* extract.
Figure 14:
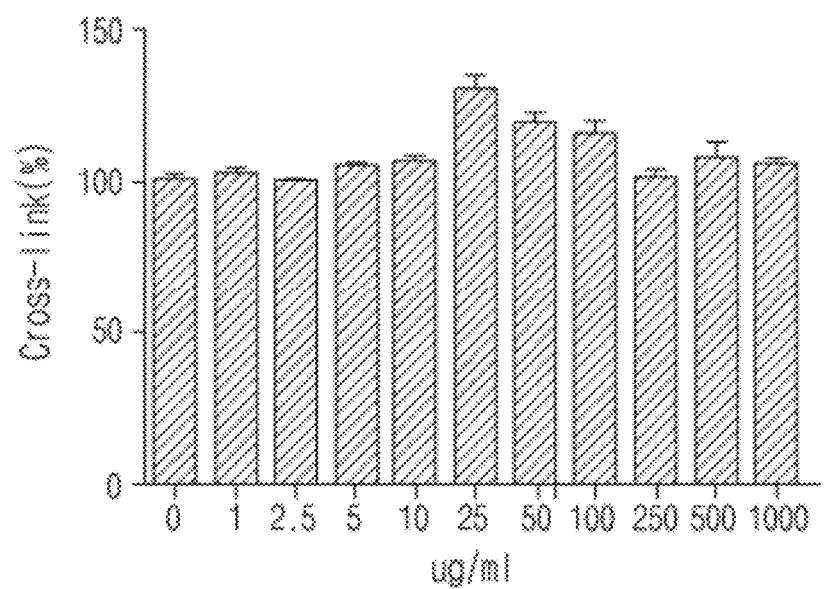
FIG. 14 is a graph illustrating the AGE-BSA breaking effect of ethyl acetate layer of *Osteomeles schwerinae* extract.

3. Evaluation of Inhibition or Breaking Effect on Advanced Glycation Endproducts (AGEs) Cross-Link Inhibition effect (see Table 4) or breaking effect (see Table 5) of *Osteomeles schwerinae* small twig/leaf extract and its fractions cultured for 28 days on advanced glycation endproducts (AGEs) cross-link was as follows. FIG. 9 and FIG. 10 are graphs illustrating the AGE-BSA inhibition and breaking effect of *Osteomeles schwerinae* small twig/leaf extract. As shown herein, *Osteomeles schwerinae* small twig/leaf extract demonstrated the both inhibition and breaking effect, and particularly inhibition effect was more significant. FIG. 11 is a graph illustrating the AGE-BSA inhibition effect of hexane layer of *Osteomeles schwerinae* extract, and FIG. 12 is a graph illustrating the AGE-BSA breaking effect of hexane layer of *Osteomeles schwerinae* extract. As shown herein, hexane layer of *Osteomeles schwerinae* extract demonstrated the both inhibition and breaking effect, and particularly inhibition effect was more significant. FIG. 13 is a graph illustrating the AGE-BSA inhibition effect of ethyl acetate layer of *Osteomeles schwerinae* extract, and FIG. 14 is a graph illustrating the AGE-BSA breaking effect of ethyl acetate layer of *Osteomeles schwerinae* extract. As shown herein, ethyl acetate layer of *Osteomeles schwerinae* extract had no breaking effect but showed excellent inhibition effect.

TABLE 4

| | Conc (μg/ml) | | | | | |
|---|---|---|---|---|---|---|
| | 0 | 1 | 2.5 | 5 | 10 | 25 |
| Example 1 (FIG. 9) | 100.00 ± 8.34 | 101.79 ± 3.78 | 87.75 ± 4.17 | 90.37 ± 2.90 | 99.68 ± 3.26 | 81.57 ± 11.03 |
| Example 2 (FIG. 11) | 100.00 ± 3.04 | 96.78 ± 4.07 | 100.57 ± 3.18 | 107.74 ± 3.58 | 111.05 ± 3.49 | 97.05 ± 4.06 |
| Example 3 (FIG. 13) | 100.00 ± 5.29 | 103.34 ± 7..21 | 111.19 ± 8.81 | 106.87 ± 4.98 | 107.88 ± 8.01 | 104.48 ± 13.02 |
| Example 4 (FIG. 15) | 100.00 ± 5.79 | 96.09 ± 3.14 | 95.64 ± 3.22 | 99.00 ± 4.06 | 89.61 ± 1.99 | 86.12 ± 5.98 |
| Example 5 (FIG. 17) | 100.00 ± 6.27 | 87.95 ± 4.47 | 87.88 ± 3.12 | 87.44 ± 7.19 | 93.08 ± 6.51 | 86.76 ± 2.59 |

| | Conc (μg/ml) | | | | | |
|---|---|---|---|---|---|---|
| | 50 | 100 | 250 | 500 | 1000 | $IC_{50}$ |
| Example 1 (FIG. 9) | 36.88 ± 5.51 | 40.43 ± 7.44 | 42.74 ± 7.74 | 24.82 ± 3.72 | 21.27 ± 0.93 | 63.73 ± 16.62 |
| Example 2 (FIG. 11) | 60.29 ± 5.93 | 22.49 ± 2.34 | 22.89 ± 3.90 | 29.62 ± 3.03 | 20.97 ± 0.96 | 68.65 ± 2.75 |
| Example 3 (FIG. 13) | 95.04 ± 12.96 | 65.40 ± 10.21 | 48.91 ± 17.96 | 41.22 ± 8.38 | 29.95 ± 3.66 | 370.94 ± 102.81 |
| Example 4 (FIG. 15) | 72.06 ± 9.26 | 80.14 ± 20.67 | 36.55 ± 3.88 | 28.20 ± 2.21 | 17.38 ± 0.91 | 259.26 ± 69.18 |
| Example 5 (FIG. 17) | 69.69 ± 3.38 | 58.26 ± 9.28 | 37.90 ± 5.85 | 25.85 ± 2.00 | 21.27 ± 1.28 | 170.56 ± 30.12 |

TABLE 5

| | Conc (μg/ml) | | | | | |
|---|---|---|---|---|---|---|
| | 0 | 1 | 2.5 | 5 | 10 | 25 |
| Example 1 (FIG. 10) | 100.00 ± 7.18 | 96.43 ± 2.74 | 98.99 ± 7.68 | 100.15 ± 5.08 | 100.64 ± 4.40 | 89.75 ± 4.64 |
| Example 2 (FIG. 12) | 100.00 ± 1.10 | 101.61 ± 3.36 | 99.28 ± 5.00 | 107.00 ± 10.37 | 104.67 ± 9.98 | 105.15 ± 3.99 |
| Example 3 (FIG. 14) | 100.00 ± 3.54 | 102.24 ± 3.41 | 99.81 ± 1.59 | 104.58 ± 1.65 | 106.16 ± 3.30 | 129.90 ± 9.99 |
| Example 4 (FIG. 16) | 100.00 ± 7.21 | 95.59 ± 6.06 | 98.81 ± 9.44 | 96.32 ± 4.58 | 84.28 ± 4.33 | 59.19 ± 2.51 |
| Example 5 (FIG. 18) | 100.00 ± 3.56 | 103.78 ± 5.67 | 105.07 ± 5.01 | 103.98 ± 1.05 | 108.65 ± 9.50 | 82.50 ± 3.21 |

| | Conc (μg/ml) | | | | | |
|---|---|---|---|---|---|---|
| | 50 | 100 | 250 | 500 | 1000 | $IC_{50}$ |
| Example 1 (FIG. 10) | 70.18 ± 4.29 | 59.78 ± 10.41 | 53.22 ± 10.41 | 36.91 ± 9.88 | 28.32 ± 5.08 | 283.98 ± 148.4 |
| Example 2 (FIG. 12) | 103.94 ± 4.20 | 98.95 ± 15.33 | 76.27 ± 2.49 | 59.77 ± 2.16 | 43.93 ± 3.26 | 828.89 ± 43.53 |
| Example 3 (FIG. 14) | 118.97 ± 5.72 | 114.76 ± 8.81 | 100.37 ± 5.38 | 106.72 ± 10.27 | 104.58 ± 4.19 | >1000 |
| Example 4 (FIG. 16) | 61.31 ± 15.28 | 48.44 ± 2.67 | 39.10 ± 5.80 | 34.01 ± 5.83 | 34.28 ± 2.15 | 117.79 ± 35.83 |
| Example 5 (FIG. 18) | 58.55 ± 4.78 | 52.29 ± 3.82 | 33.70 ± 1.90 | 31.91 ± 3.40 | 31.61 ± 1.51 | 107.94 ± 20.60 |

Figure 15:
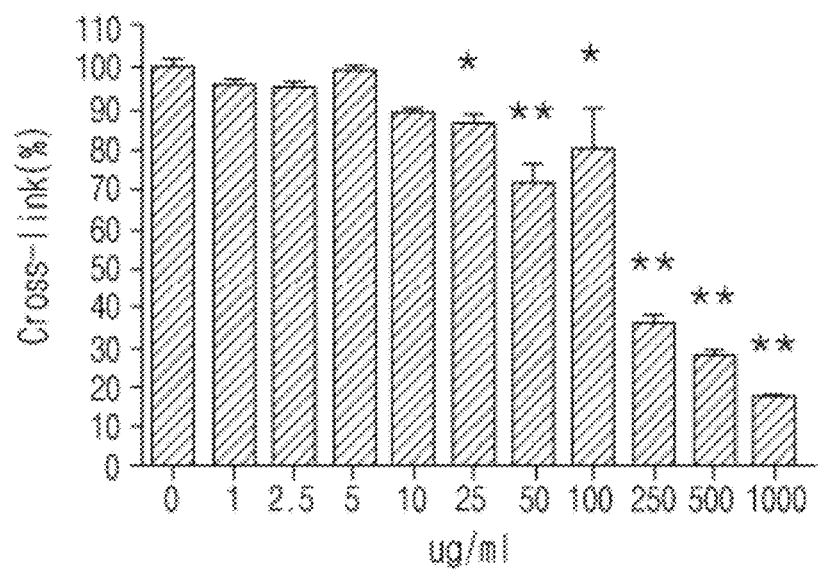
FIG. 15 is a graph illustrating the AGE-BSA inhibition effect of butanol layer of *Osteomeles schwerinae* extract.
Figure 16:
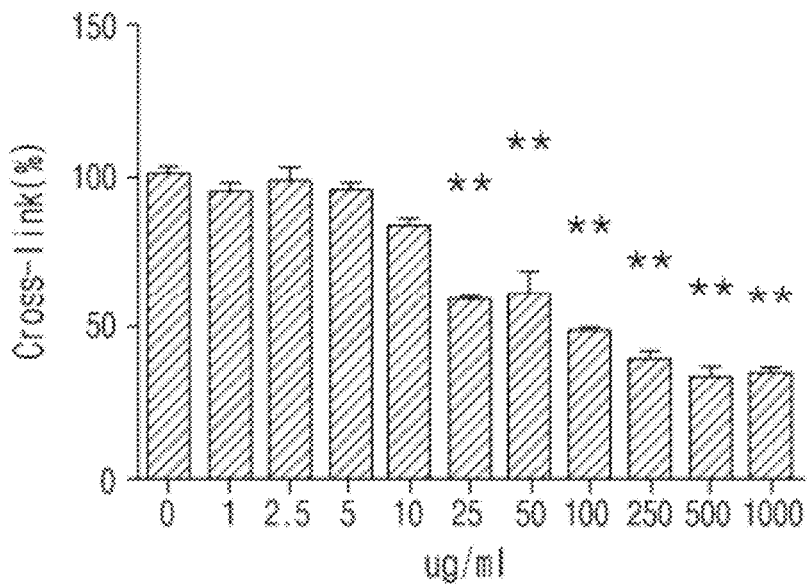
FIG. 16 is a graph illustrating the AGE-BSA breaking effect of butanol layer of *Osteomeles schwerinae* extract.

FIG. 15 is a graph illustrating the AGE-BSA inhibition effect of butanol layer of *Osteomeles schwerinae* extract, and FIG. 16 is a graph illustrating the AGE-BSA breaking effect of butanol layer of *Osteomeles schwerinae* extract. As shown herein, butanol layer of *Osteomeles schwerinae* extract demonstrated the both inhibition and breaking effect.

Figure 17:
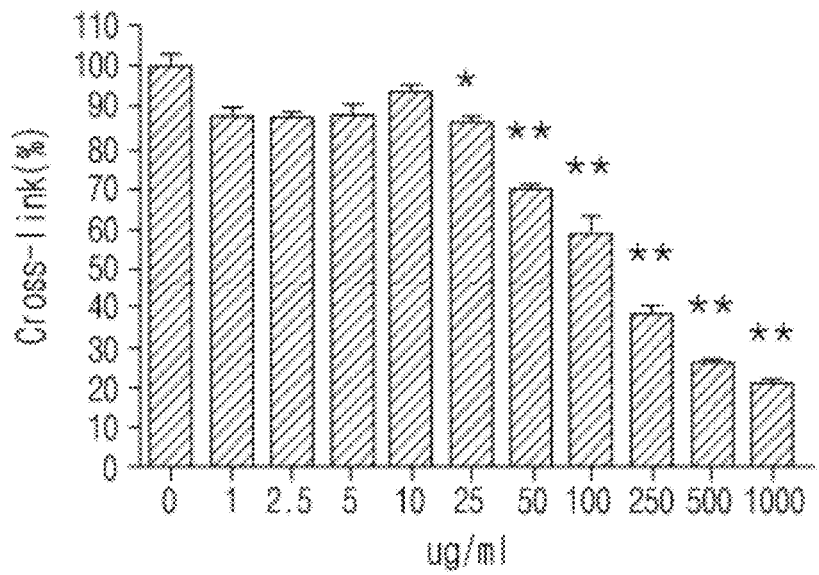
FIG. 17 is a graph illustrating the AGE-BSA inhibition effect of water layer of *Osteomeles schwerinae* extract.
Figure 18:
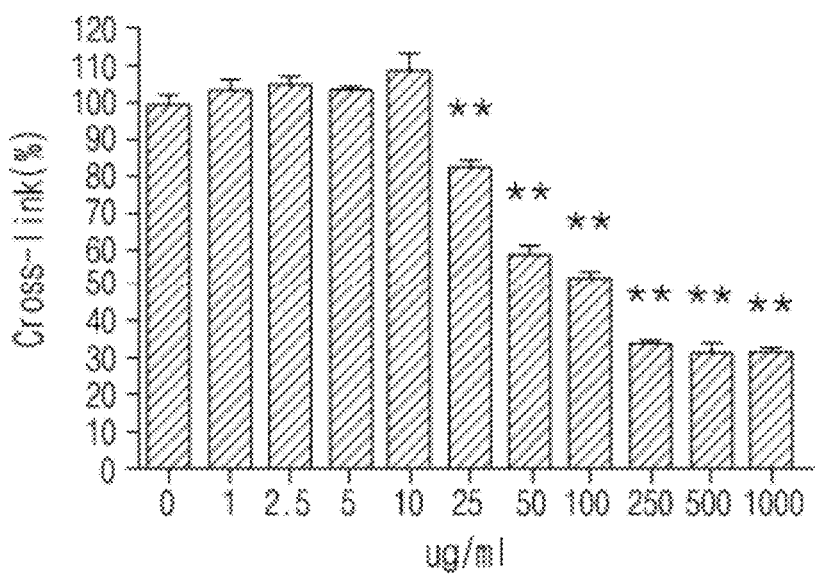
FIG. 18 is a graph illustrating the AGE-BSA breaking effect of water layer of *Osteomeles schwerinae* extract.

FIG. 17 is a graph illustrating the AGE-BSA inhibition effect of water layer of *Osteomeles schwerinae* extract, and FIG. 18 is a graph illustrating the AGE-BSA breaking effect of water layer of *Osteomeles schwerinae* extract. As shown herein, water layer of *Osteomeles schwerinae* extract demonstrated the both inhibition and breaking effect.

Experimental Example 2

Analysis of Inhibitory Effect on Aldose Reductase Activity

<2-1> In Vitro Analysis of Inhibitory Effect of *Osteomeles schwerinae* Small Twig/Leaf Extract and its Fractions Obtained from Each of Hexane Layer, Ethyl Acetate Layer, Butanol Layer and Water Layer on Aldose Reductase Activity To obtain natural aldose reductase from eyeballs of SD rat (Sprague-Dawley rat, 250-280 g) by the method of Dufrane (1984), the extracted lens were pulverized together with 135 mM Na, K-phosphate buffer (pH 7.0), and 10 mm 2-mercaptoethanol using homogenizer and sonicater. After performing centrifugation at 14000 rpm for 30 minutes, the supernatant was filtered with 0.2 μm filter at 4° C. Quantification was performed by Lowry method using BSA as a protein source of enzyme. The mixture of 135 mM Na, K-phosphate buffer (pH 7.0), 100 mM lithium sulfate, 0.03 mM NADPH, 0.04 mM DL-glyceraldehyde and 100 μg/ml enzyme was dissolved in 0.1% DMSO, which was added to 50 μl of each sample diluted at different concentrations. Total volume of the mixture was adjusted to 1 ml, followed by reaction at 37° C. for 10 minutes. BLK was treated with the mixture which did not contain 0.04 mM DL-glyceraldehyde, while STD was treated with the mixture comprising 135 mM Na, K-phosphate buffer (pH 7.0), 100 mM lithium sulfate and 50 μl NADP (0.2-5 μM). The reaction was terminated by adding 0.3 ml of 0.5 N HCl, to which 1 in of 6 M NaOH supplemented with 10 mM imidazole wad added, followed by reaction at 60° C. for 10 minutes. Then, conversion rate (NADP fluorescent product) was measured. Each sample was tested in triplicate. Inhibition effect was measured by using spectrofluorophotometric detector (Ex. 360 nm, Em. 460 nm, Bio-TEK, Synergy HT, USA) and the results were presented as $IC_{50}$. *Osteomeles schwerinae* small twig/leaf extract was prepared at different concentrations of 1 μg/ml, 2.5 μg/ml and 5 μg/l. Hexane layer was prepared at different concentrations of 2.5 μg/ml, 5 μg/ml and 10 μg/ml. Ethyl acetate layer was prepared at different concentrations of 0.25 μg/ml, 0.5 μg/ml and 1 μg/ml. Butanol layer was prepared at different concentrations of 2.5 μg/ml, 5 μg/ml and 10 μg/ml. Water layer was prepared at different concentrations of 20 μg/ml, 30 μg/ml and 40 μg/ml. For the comparative control group, one of the excellent aldose reductase inhibitors, 3,3-tetramethyleneglutaric acid, was prepared at different concentrations of 3.72 μg/ml, 4.66 μg/ml and 5.59 μg/ml, which were used for the measurement of inhibitory effect on aldose reductase activity. The inhibitory effect on aldose reductase activity was measured in vitro by the same manner as described above and the results are shown in Table 6.

TABLE 6

| Compound/effect | Concentration (μg/ml) | Inhibitory effect (%) | inhibitory effect ($IC_{50}$, μg/ml) |
|---|---|---|---|
| extract of *Osteomeles schwerinae* small twigs and leaves | 1 | 30.63 ± 7.42 | 3.20 |
| | 2.5 | 41.55 ± 1.62 | |
| | 5 | 67.61 ± 3.23 | |
| hexane fraction of *Osteomeles schwerinae* twig/leaf extract | 2.5 | 26.67 ± 4.84 | 7.26 |
| | 5 | 41.11 ± 3.33 | |
| | 10 | 62.22 ± 4.84 | |
| ethyl acetate fraction of *Osteomeles schwerinae* | 0.25 | 20.48 ± 1.20 | 0.95 |
| | 0.5 | 26.91 ± 3.68 | |

TABLE 6-continued

| Compound/effect | Concentration (µg/ml) | Inhibitory effect (%) | inhibitory effect (IC$_{50}$, µg/ml) |
|---|---|---|---|
| twig/leaf extract | 1 | 53.01 ± 6.71 | |
| butanol fraction of | 2.5 | 35.5 ± 4.63 | 5.81 |
| Osteomeles schwerinae | 5 | 45.8 ± 0.66 | |
| twig/leaf extract | 10 | 69.08 ± 0 | |
| water fraction of | 20 | 42.14 ± 3.80 | 24.93 |
| Osteomeles schwerinae | 30 | 57.23 ± 5.15 | |
| twig/leaf extract | 10 | 76.59 ± 3.52 | |
| 3,3-tetramethyleneglutaric acid | 3.72 (20 µm) | 39.34 ± 4.17 | 4.50 (24.14 µm) |
| | 4.66 (25 µm) | 55.74 ± 3.25 | |
| | 5.59 (30 µm) | 60.33 ± 1.39 | |

As shown in table 6, inhibitory effect of *Osteomeles schwerinae* small twig/leaf extract on aldose reductase activity was excellent (IC$_{50}$: 3.20 µg/ml), which was greater than that of the positive control, 3,3-tetramethyleneglutaric acid (IC$_{50}$: 4.50 µg/ml). In the case of the fractions, inhibitory effect of ethyl acetate layer (IC$_{50}$: 0.95 µg/ml) was 5 times higher than that of the positive control. Therefore, the *Osteomeles schwerinae* extract and its fractions of the present invention, particularly the ethyl acetate fraction, were confirmed to have excellent inhibitory effect on aldose reductase activity. In addition, other fractions, hexane layer, butanol layer and water layer, also had excellent inhibitory effect on aldose reductase activity compared with the single synthetic compound. Therefore, it was suggested that the *Osteomeles schwerinae* extract and its fractions of the present invention can contribute to the development of a novel treatment agent for diabetic complications and related diseases thereof.

Experimental Example 3

Analysis of Anti-Oxidative Effect

Anti-oxidative effect of *Osteomeles schwerinae* small twig/leaf extract, fractions thereof obtained from each of hexane layer, ethyl acetate layer, butanol layer and water layer of the extract was investigated in vitro. Free radical scavenging activity of each sample was measured by DPPH method (Brand-Williams W, et al., *Technology*, 1995, 28, 25-30). Samples were dissolved in ethanol, and diluted at different concentrations. Each of the diluted sample was distributed in 96 well plate (20 µl/well). 100 mM DPPH solution dissolved in ethanol was added to each well by 180 µl to make the final volume of the reaction solution 200 µl, followed by reaction at room temperature for 30 minutes. Then, OD$_{517}$ was measured with ELISA reader (Bio-TEK, Synergy HT, USA) to investigate absorbance changes by reduction of DPPH. Free radical scavenging activity was presented as RC$_{50}$, which is the amount of sample (µg/ml) needed for the reduction of 50% DPPH. For the positive control, butylated hydroxytoluene (BHT) was used. Anti-oxidative effect of *Osteomeles schwerinae* small twig/leaf extract was measured in vitro by the same manner as described above and the results are shown in Table 7.

TABLE 7

| Sample | RC$_{50}$ (µg/ml) |
|---|---|
| *Osteomeles schwerinae* ethanol extract | 8.46 ± 1.47 |
| Hex layer | 41.88 ± 11.61 |
| EA layer | 7.54 ± 1.55 |
| BuOH layer | 11.98 ± 5.46 |

TABLE 7-continued

| Sample | RC$_{50}$ (µg/ml) |
|---|---|
| Water layer | 15.68 ± 8.89 |
| BHT (positive control) | 26.75 ± 10.75 |

As shown in Table 7, it was confirmed that *Osteomeles schwerinae* small twig/leaf extract and its fractions, except hexane layer, had excellent anti-oxidative effect.

Experimental Example 4

Ex Vivo Analysis of Anti-Cataract Effect

Following experiment was performed to investigate ex vivo anti-cataract effect of *Osteomeles schwerinae* small twig/leaf extract. Stock solution of the extract of the present invention was dissolved (1000x) in DMSO (Sigma, USA), which was then filtered with 0.22 µm filter (syringe filter) (Millipore, USA). For the positive control, Epalrestat was used. For organ culture of lens, Sprague-Dawley mouse (4 weeks old, 200 g) was used. The animal was sacrificed by cervical spine fracture. Eyeballs were extracted and placed in 1.5 ml tube containing 1 ml of PBS (Welgen, USA). Lens was carefully separated from the eyeball by posterior approach. Then, iris and zonule were eliminated. Those lenses without surgical damage were selected for the experiment (Spector et al., *Exp. Eye Research*, 1993, 57, 656-667). The lenses were loaded in each well of 24 well plate (Nalgen Nunc, Denmark) containing 1 ml of medium 199 (Gibco, USA) supplemented with 5 mg/L gentamycin (Gibco, USA) and 0.5 mg/L fungizione (Gibco, USA). After treating the extract and its fractions of the present invention, the plate was cultured in 5% CO$_2$, 95% air atmosphere, at 37° C. for 4 days (Bradford, M., *Analytical Biochemistry*, 1976, 72, 248-254). Sugar cataract was induced by adding 20 mM xylose (Aldrich, USA). For the positive control, 1 µg/ml or 3 uM epalrestat was treated before culture (Obazawa H., et al., *Invest. Opthalmol*, 1974, 13, 204). To measure the lens opacity, the cultured lens was observed under optical microscope connected with CCD camera for 4 days (Chand et al., *Exp. Eye Research*, 1982, 35, 491-497). Lens opacity was measured by Scion image analyzer (Scion Corporation, USA) and the measured value was presented by arbitrary units (AU) per pixel. Anti-cataract effect of *Osteomeles schwerinae* small twig/leaf extract and its fractions (hexane layer, ethyl acetate layer, butanol layer and water layer) was measured ex vivo by the same manner as described above. The results of the extract are shown in FIG. 19 and FIG. 20, and the results of the fractions are shown in FIG. 21 and FIG. 22.

FIG. 19 is a set of photographs illustrating the anti-cataract effect of *Osteomeles schwerinae* small twig/leaf extract in the ex vivo mouse lens. FIG. 20 is a graph illustrating the anti-cataract effect of *Osteomeles schwerinae* small twig/leaf extract in the ex vivo mouse lens. As shown herein, the experimental group treated with 10 µg/ml of *Osteomeles schwerinae* small twig/leaf extract demonstrated significant anti-cataract effect on day 3, compared with the group induced cataract with xylose on day 3 (p<0.01, *p<0.001 vs. the group induced cataract with xylose).

FIG. 21 is a set of photographs illustrating the anti-cataract effect of fractions of *Osteomeles schwerinae* small twig/leaf extract in the ex vivo mouse lens. FIG. 22 is a graph illustrating the anti-cataract effect of fractions of *Osteomeles schwerinae* small twig/leaf extract in the ex vivo mouse lens. As shown herein, all the experimental groups treated with 5

µg/ml of fractions of *Osteomeles schwerinae* small twig/leaf extract demonstrated significant anti-cataract effect on day 3, compared with the group induced cataract with xylose on day 3 (*p<0.05, p<0.01, *p<0.001 vs. the group induced cataract with xylose).

Experimental Example 5

Efficacy Analysis in Diabetes Animal Model

Treatment and postponement effects of *Osteomeles schwerinae* extract on diabetic nephropathy, retinopathy and cataract in type I and type II diabetes animal models were investigated.

<5-1> Efficacy Test in Type I Diabetes Animal Model
<5-1-1> Inducement of Type I Diabetes, Raising the Animal, and Experimental Procedure Fully adapted (for 1 week) SD rats (6 weeks, 180-200 g) were used. After adaptation, the rats were fasted for 16 hours. Before the administration of samples, streptozotocin dissolved in 0.1 M citrate buffer (pH 4.5) was treated once by peritoneal injection (60 mg/kg). A week after the peritoneal injection, blood glucose level was measured at fasted or non-fasted state. Rats showing blood glucose level of at least 250 mg/dl at fasted state were selected and distributed fairly with considering the average. 5 groups were prepared as follows: the normal group treated with nothing (presented as Nor), the normal group treated with 200 mg/kg of *Osteomeles schwerinae* extract (presented as N+OS-141), the group induced with diabetes (presented as DM), the diabetes group treated with 100 mg/kg of *Osteomeles schwerinae* extract (presented as OS-100), and the positive control group treated with aminoguanidine (presented as AG). *Osteomeles schwerinae* extract and aminoguanidine were dissolved in water, which were administered orally to the rats every day (5 ml/kg) for 8 weeks. 8 weeks later, the animals were fasted, followed by autopsy. Blood was drawn from saphenons vein. Plasma was separated by centrifuging the whole blood at 3000 rpm at 4° C. The plasma was stored at −70° C. for the later use for data analysis. Each organ was weighed and frozen by using liquid nitrogen, which was stored at 70° C.

1. Weight Change

Weight was compared between the normal group and the group treated with *Osteomeles schwerinae* extract and the result indicated that there was no significant difference in weights, which also suggested that *Osteomeles schwerinae* extract had no toxicity. However, weight of the diabetes group was significantly reduced. Weight was compared between the diabetes group not treated and the diabetes group treated with the extract of the present invention, and the result indicated that there was no significant difference in weights between the two groups (see Table 8).

TABLE 8

| Group | Body weight (g) | |
|---|---|---|
| | Initial | Final |
| Nor | 301.3 ± 10.4 | 475.9 ± 10.7 |
| N + OS-200 | 304.4 ± 6.6 | 457.6 ± 11.1 |
| DM | 243.1 ± 1.89 | 208.5 ± 12.1** |
| AG | 244.3 ± 4.02 | 210.3 ± 9.98 |
| OS-100 | 241.0 ± 5.04 | 195.4 ± 11.67 |

* Table 8 illustrates the changes of body weight and organ weight in type I diabetes animal model.

Nor: normal rat

N + OS-200: normal rat treated with 200 mg/kg of *Osteomeles schwerinae* extract DM: diabetes animal model AG: aminoguanidine OS-100: diabetes animal model treated with 100 mg/kg of *Osteomeles schwerinae* extract All data expressed as mean ± SD.

**p < 0.01 vs Nor.

2. Blood Biochemical Change

AST and ALT were compared between the normal group not treated and the group treated with *Osteomeles schwerinae* extract, and the result indicated that there was no significant difference between the two groups. This result suggested that *Osteomeles schwerinae* extract had no hepatotoxicity. In the meantime, AST and ALT in the diabetes group were significantly increased. However, the group treated with *Osteomeles schwerinae* extract demonstrated significantly reduced AST and ALT (see Table 9).

TABLE 9

| | Nor | N + OS | DM | AG | OS-100 |
|---|---|---|---|---|---|
| AST (U/L) | 177.8 ± 23.63 | 169.9 ± 15.54 | 487.3 ± 104.3** | 341.6 ± 70.90 | 245.1 ± 32.70# |
| ALT (U/L) | 50.16 ± 10.57 | 55.48 ± 8.07 | 235.1 ± 49.71** | 158.9 ± 26.25 | 108.4 ± 12.63# |

* Table 9 illustrates the blood biochemical changes in type I diabetes animal model.

All data are expressed as mean ± SD.

**p < 0.01 vs Nor, p < 0.05 vs DM.

<5-1-2> Effect on Diabetic Nephropathy

1. Changes of Renal Function Indices

Urine was taken for 24 hours on the last week before autopsy to comparatively observe renal function indices and oxidative stress factors. ELISA was performed to measure AGEs and podocyte (synaptopodin). Urine was mixed with coating buffer (50 mM carbonate buffer, pH 9.6) at the ratio of 1:2, which was distributed in 96 well plate (100 µl/well). After incubating the plate at 37° C. for 3 hours, the plate was washed with 0.05% PBST three times, and blocked with 3% skim milk. The plate was stood for one hour and then washed. AGEs (Transgenic, Japan) and synaptopodin (Santa Cruz, USA) antibody were diluted at the ratio of 1:1000 respectively, followed by loading in each well of the plate by 100 µl, which stood at 37° C. for 2 hours. After washing the plate with 0.05% PBST, HRP-conjugated 2nd antibody was loaded in each well of the plate by 100 µl, which stood at 37° C. for 1 hour. 3,3',5,5'-tetramethylbenzidine (TMB) was added in each well of the plate by 100 µl. Five minutes later, reaction termination solution (1M $H_2SO_4$) was added in each well of the plate by 100 μl and then OD was measured with ELISA reader. Albuminuria and creatinine (Cr) used as renal function indices were measured. Urine alb/Cr was significantly increased in the diabetes group, compared with that in the normal group. In the meantime, the level was decreased in the group treated with AG or *Osteomeles schwerinae* extract significantly, compared with that in the diabetes group. Albuminuria was also significantly increased in the diabetes group, compared with that in the normal group but decreased significantly in the group treated with AG or *Osteomeles schwerinae* extract, compared with that in the diabetes group (see FIG. 23).

2. Histopathological Staining

Kidney was extracted during autopsy, which was fixed in 10% neutralized formalin, followed by dehydration. The kidney was substituted with xylene three times, followed by embedding with paraffin. The embedded tissue block was cut into 4 μm sections, which were placed on microscope slide. PAS staining was performed to observe morphological changes. The stained slide was observed under optical microscope. After PAS staining, it was observed that glomerular basement membrane thickening, mesangial matrix enlargement, glomerular hypertrophy and glomerulosclerosis caused by extracellular substrate accumulation were observed in the diabetes group even though they were not significant compared with the normal group. The group treated with *Osteomeles schwerinae* extract did not show any difference from the normal group. In the diabetes group treated with AG or *Osteomeles schwerinae* extract, any change in glomerular basement membrane thickening was not observed, compared with the diabetes group not treated with the extract. To investigate fibrosis by collagen infiltrated in kidney cortex, Masson's trichrome staining was performed. Multiple numbers of collagen stained as blue by Masson's trichrome were observed around glomerular, basement membrane and in interstitial area between renal tubules in the diabetes group, but the difference was not significant from that of the normal group. Also, such change was not peculiar in the diabetes group treated with AG or *Osteomeles schwerinae* extract. Histological changes were traced 8 weeks after inducing diabetes. As a result, basement thickening or fibrosis by collagen, which are usually observed in renal complications, were not significant, suggesting that the stage of diabetic nephropathy was in the early stage (see FIG. 24).

3. Changes of Podocyte Loss

Staining of synatopodin (cytoplasm), the podocyte marker, and WT1 was performed to investigate podocyte loss in glomerulus. As a result, podocyte loss was significant in the diabetes group, compared with the normal group. In the meantime, the normal group treated with *Osteomeles schwerinae* extract did not show much difference from the normal group. In the group treated with 100 mg/kg of AG and *Osteomeles schwerinae* extract, podocyte loss was reduced compared with that in the diabetes group (see FIG. 25).

4. Changes of AGEs and RAGE Expressions in Kidney

The expressions of AGEs and RAGE were reduced in the normal group treated with *Osteomeles schwerinae* extract, compared with the normal group, but significantly increased in the diabetes group. In the group treated with 100 mg/kg of AG and *Osteomeles schwerinae* extract, the expressions of AGEs and RAGE were significantly reduced (see FIG. 26).

5. Anti-Oxidative Effect in Kidney

Anti-oxidation level in the kidney was not much different between the normal group treated with *Osteomeles schwerinae* extract and the normal group not treated. However, when the normal group was compared with the diabetes group, 8-OHdG was significantly increased in the diabetes group, suggesting that oxidative stress was increased in the diabetes group. In the meantime, 8-OHdG was significantly reduced in the group treated with *Osteomeles schwerinae* extract, compared with the diabetes group, suggesting that the extract had excellent anti-oxidative effect. 8-OHdG was also reduced in the group treated with AG, but the decrease was not that significant (see FIG. 27).

<5-1-3> Treatment and Postponement Effect on Diabetic Retinopathy

1. Damage of Retinal Vessel Pericytes and Vascular Endothelial Cells

To investigate the damage or loss of pericytes and endothelial cells playing an important role in maintaining the functions of retinal vessels, it was investigated whether or not the pericyte ghost was generated in retinal vessels. Retina was extracted from the right eyeball and then washed with running water, followed by culture at 37° C. for 1 hour in 3% trypsin. The digested retina was transferred in PBS, from which internal membrane was eliminated. Vascular frame was separated from the retina background by using a glass rod, which was placed on the slide and dried. PAS and hematoxylin staining was performed to observe the changes of cell wall and nucleus. Small number of pericyte ghost was observed in retina vessels of the diabetes group, but no abnormal sign was observed in the group treated with *Osteomeles schwerinae* extract (100 mg/kg). TUNEL staining was also performed and caspase-3 expression was examined. As a result, multiple numbers of TUNEL positive cells and cleaved caspase-3 positive cells were observed in retinal vessels of the diabetes group. However, the above changes were significantly inhibited in the group treated with *Osteomeles schwerinae* extract (100 mg/kg) (see FIG. 28).

2. Changes in Expressions of AGEs, iNos and NF-κB Involved in Retina Vessel Cell Damage The up-regulation of iNOS and NF-κB by the accumulation of AGEs plays an important role in retina vessel cell damage. Thus, AGEs accumulation in retina vessels was investigated. As a result, a large quantity of AGEs were accumulated in cytoplasms of pericytes and endothelial cells of the diabetes group animals and accordingly the expressions of iNOS mRNA and protein were increased by the AGEs accumulation. The expression of NF-κB was also significantly increased. However, such changes were significantly inhibited in the group treated with *Osteomeles schwerinae* extract (100 mg/kg) (see FIG. 29).

<5-2> Efficacy Test in Type II Diabetes Animal Model

<5-2-1> Raising of Type II Diabetes Animal Model and Experimental Procedure

To investigate the preventive and therapeutic effect of *Osteomeles schwerinae* on diabetic complications in type II diabetes animal model, the extract was orally administered to Spontaneous Diabetic Torii (SDT) rats for 16 weeks, followed by analysis of the effect. Spontaneous Diabetic Torii (SDT) rats, the type II diabetes animal model, were used as test animals. Particularly, male SDT rats at 10 weeks (CLEA Japan Inc., Tokyo, Japan) were adapted for 1 week, and then raised for 15 weeks until high blood glucose was induced up to the level of 300 mg/dl. Feeds and water were provided freely. 15 weeks later, the rats were divided into 5 groups, 8 rats per each group. As test drugs, *Osteomeles schwerinae* extract (Os-100, OS-250) and metformin (MET, control drug) were orally administered once a day. The experimental groups were as follows: the normal group (NOR), the diabetes group (DM), the diabetes group treated with 350 mg/kg of metformin (MET), the diabetes group treated with 100 mg/kg of *Osteomeles schwerinae* extract (OS-100), and the diabetes group treated with 250 mg/kg of *Osteomeles schwerinae* extract (OS-250). Each group was orally administered with the test drug once a day for 16 weeks. Urine was taken for 24 hours before autopsy. The organs extracted from the autopsy were stored at −80° C.

<5-2-2> Treatment and Postponement Effect on Diabetic Nephropathy

1. AGEs Concentrations in Urine and Kidney

As the renal function index, the level of AGEs in urine was measured. As a result, the level was significantly increased in the diabetes group, compared with the normal group, but not significantly changed in the group treated with the control drug. The level of AGEs was significantly decreased in the group treated with *Osteomeles schwerinae* extract (at the concentrations of 100 mg/kg and 350 mg/kg), compared with the diabetes group. From the results of glomerular histological staining, it was confirmed that the accumulation of AGEs in the diabetes group was significantly increased, compared with that in the normal group. In the group treated with *Osteomeles schwerinae* extract, the accumulation was significantly reduced dose dependently (see FIG. 30).

2. Preventive Effect on Morphological Changes

The kidney was embedded in paraffin, with which slides were prepared. PAS staining was performed with the slides. From the observation after PAS staining, it was confirmed that glomerular basement membrane thickening, mesangial matrix enlargement, glomerular hypertrophy and glomerulosclerosis caused by extracellular substrate accumulation were significantly induced in the diabetes group, compared with the normal group. However, glomerular hypertrophy and mesangial matrix enlargement were significantly reduced in the group treated with *Osteomeles schwerinae* dose-dependently. In the group treated with metformin, morphological changes were reduced, which was not significant, though (see FIG. 31).

3. Preventive Effect on Podocyte Loss

Figure 32:
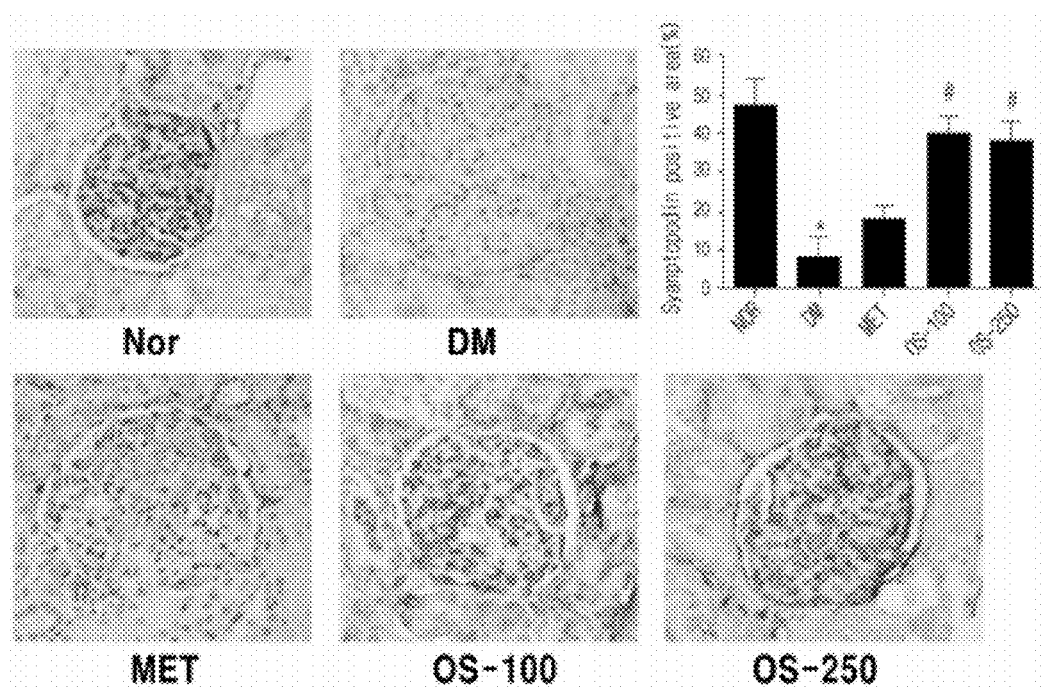
FIG. 32 is a set of photographs and a graph illustrating the preventive effect of *Osteomeles schwerinae* extract on podocyte loss in type II diabetes animal model (SDT).

Podocyte loss in glomerulus is observed in the early stage of diabetes. Thus, podocyte loss was observed by renal glomerular staining using synaptopodin, known as the podocyte marker, to investigate the effect of *Osteomeles schwerinae* extract on the prevention of podocyte loss. As a result, podocyte loss was significantly reduced in the diabetes group, compared with the normal group. There was no significant difference between the group treated with metformin and the diabetes group. However, in the group treated with *Osteomeles schwerinae* extract (at low concentration and at high concentration), podocyte loss was significantly prevented, compared with the diabetes group (FIG. 32).

<5-2-3> Treatment and Postponement Effect on Diabetic Retinopathy

1. Preventive Effect on Retinal Angiogenesis and Blood-Retinal Barrier Breaking

Figure 33:
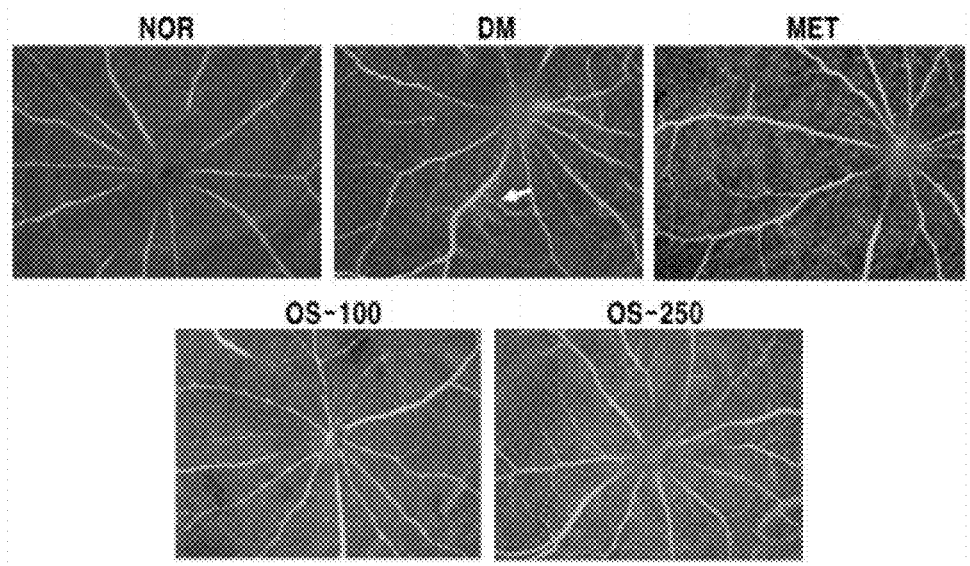
FIG. 33 is a set of photographs illustrating the anti-angiogenesis effect of *Osteomeles schwerinae* extract in type II diabetes animal model (SDT).
Figure 34:
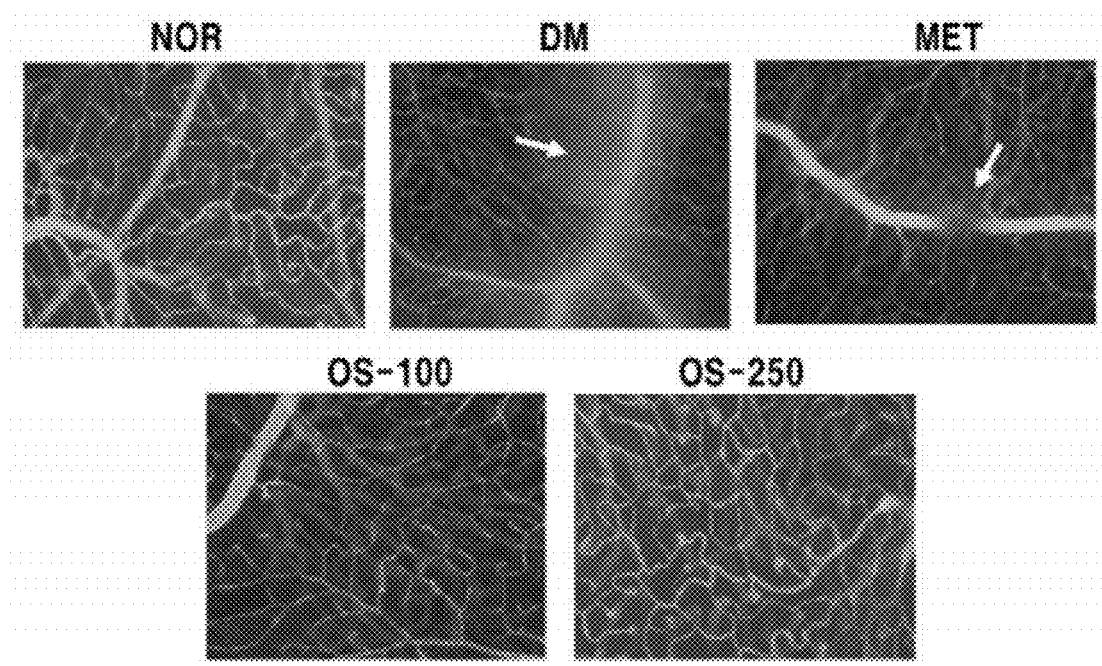
FIG. 34 is a set of photographs illustrating the preventive effect of *Osteomeles schwerinae* extract on blood retinal barrier damage in type II diabetes animal model (SDT).

The test animals were anesthetized by peritoneally injecting pentobarbital sodium (25 mg/kg body weight). Heart was extracted by opening abdominal cavity and thoracic cavity. 50 mg/ml of fluorescein-dextran ($2 \times 10^6$ molecular weight) dissolved in 1 ml/ml sterilized PBS was injected in the left ventricle. 10 minutes later, eye balls were extracted. Retina was separated from eyecup of the left eye ball. The isolated retina was placed on the slide, followed by mounting with aqueous mounting medium. The slide was completely dried and observed under fluorescent microscope. Fluorescent material was injected in retinal blood vessel, followed by observation. As a result, as shown in FIG. 33, any abnormal sign was not observed in the normal group showing even blood vessel distribution. In the meantime, angiogenesis was observed in the diabetes group (arrow). Angiogenesis was also observed in the group treated with metformin, which was not significant, though. However, angiogenesis was significantly inhibited in the group treated with *Osteomeles schwerinae* extract (both at low concentration and at high concentration). To investigate blood-retinal barrier damage, outflow of the fluorescent material was observed. As a result, as shown in FIG. 34, outflow of the fluorescent material was not observed in the normal group. However, the fluorescent material was leaked out of blood vessels, indicating blood-retinal barrier damage, in multiple animals of the diabetes group (arrow), and non-perfusion area (arrow) caused by the blood vessel being narrow was also observed in some of those animals in the diabetes group. In the group treated with metformin, outflow of the fluorescent material was observed just barely but not observed at all in the group treated with *Osteomeles schwerinae* extract (see FIG. 34).

Figure 35:
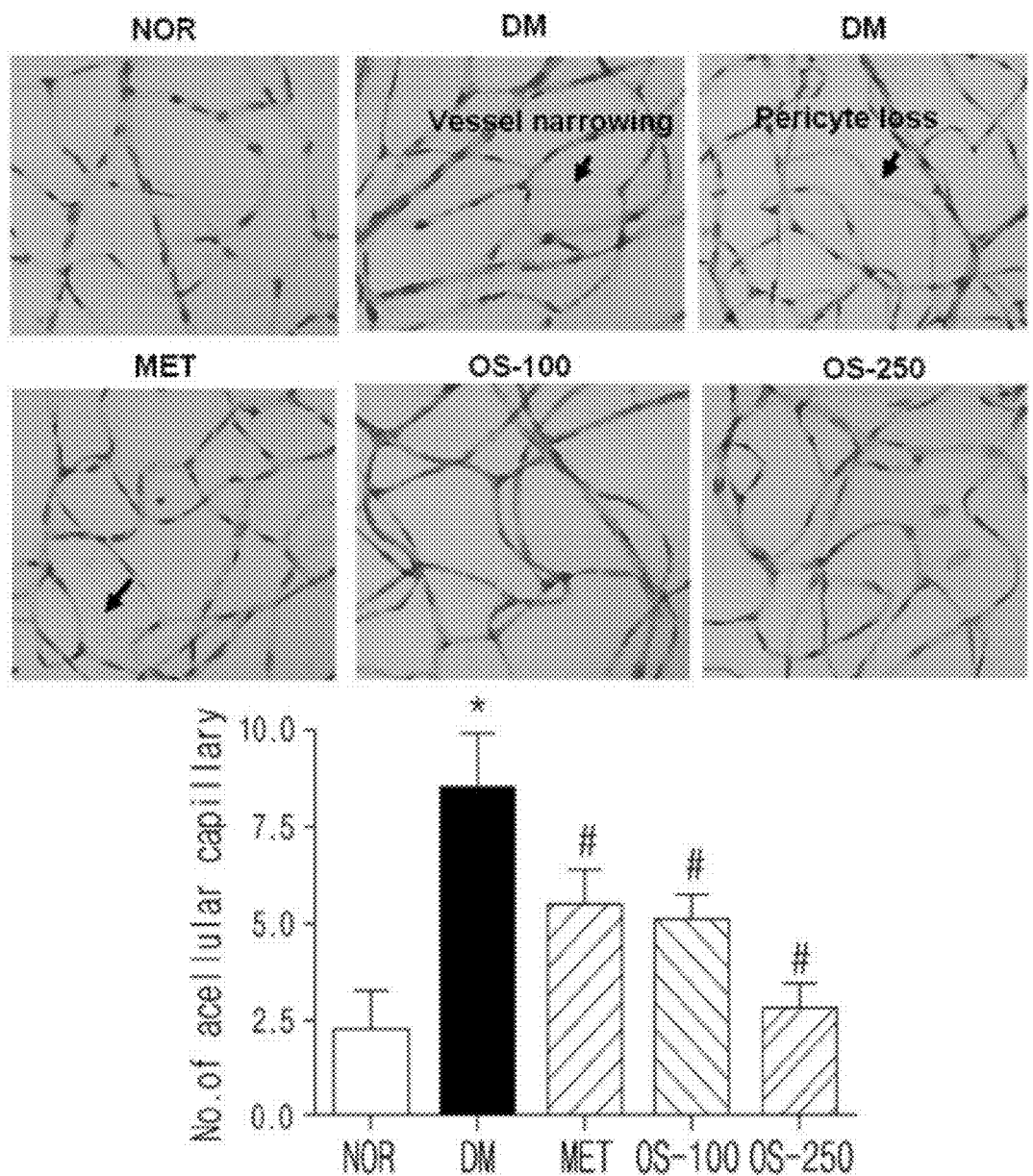
FIG. 35 is a set of photographs and a graph illustrating the preventive effect of *Osteomeles schwerinae* extract on vascular pericyte loss and acellular capillary formation in type II diabetes animal model (SDT).

2. Preventive Effect on Vascular Pericyte Loss and Acellular Capillary Formation Changes of retinal blood vessel cells accompanied by diabetic retinopathy were observed. Acellular capillary formation accompanying pericyte loss and vascular endothelial loss, and closed vessels were usually observed. As shown in FIG. 35, pericyte loss, acellular capillary formation and closed vessels were significantly increased in the diabetes group, but were significantly inhibited in the groups treated with metformin and *Osteomeles schwerinae* extract (see FIG. 35).

Figure 36:
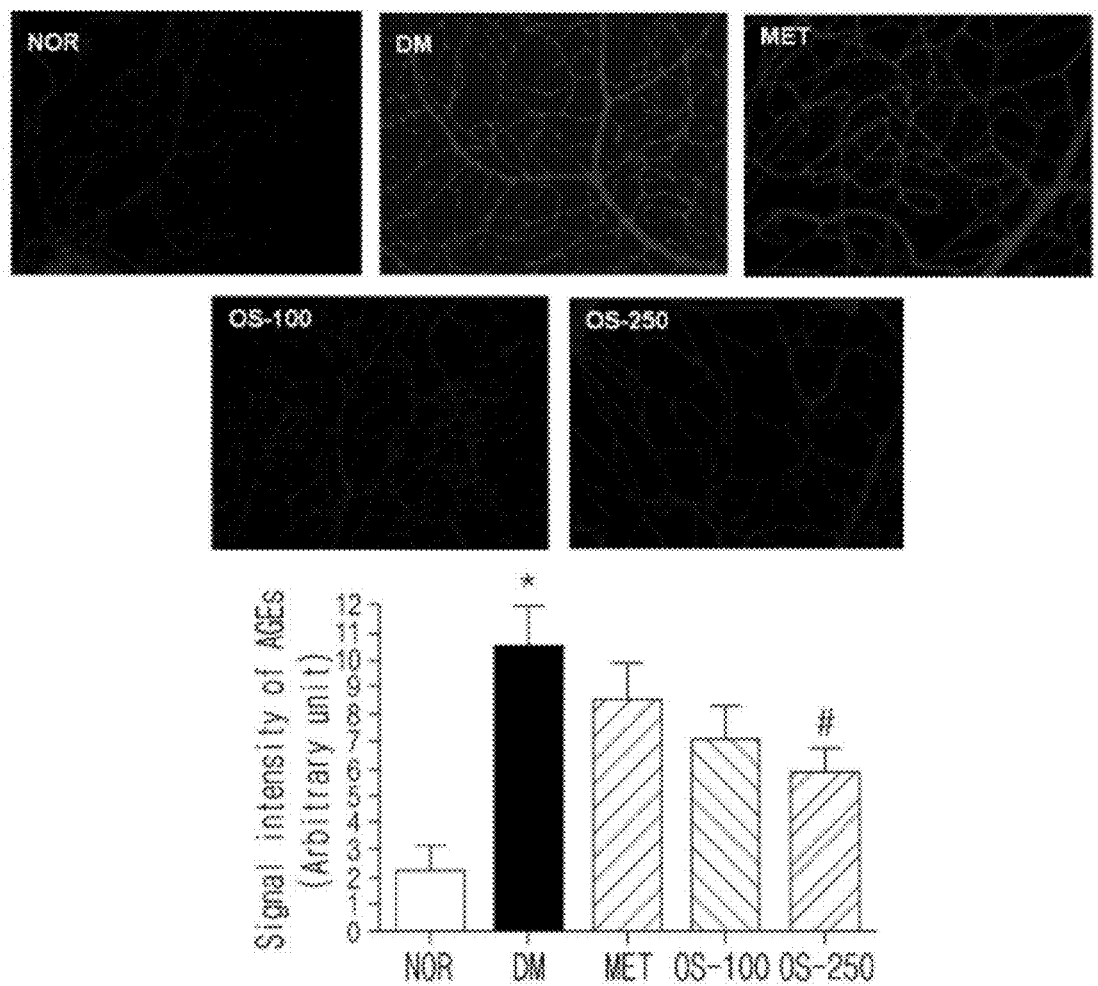
FIG. 36 is a set of photographs and a graph illustrating the preventive effect of *Osteomeles schwerinae* extract on advanced glycation endproduct accumulation in retinal blood vessel in type II diabetes animal model (SDT).

3. Preventive Effect on Advanced Glycation Endproducts Accumulation in Retinal Blood Vessels The accumulation of ACEs, the causing factor of diabetic complications, was observed in retinal blood vessels. As a result, as shown in FIG. 36, the accumulation of AGEs in retinal blood vessels was increased in the diabetes group, compared with that in the normal group. In the group treated with *Osteomeles schwerinae* extract, particularly at high concentration, the accumulation of AGEs was significantly inhibited (see FIG. 36).

4. Preventive Effect on Muller Cell Activation

Figure 37:
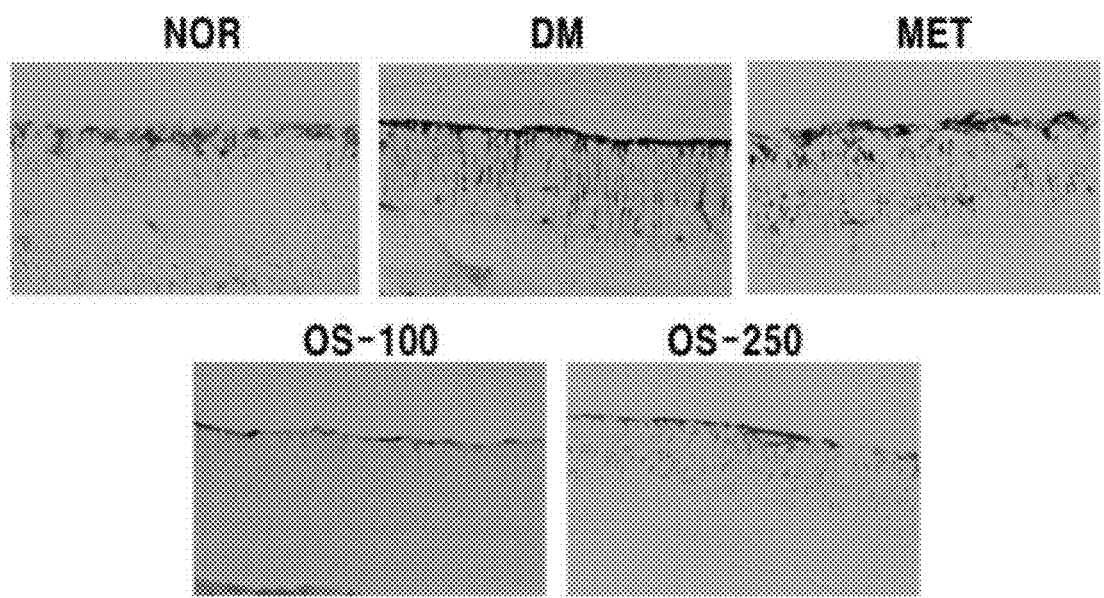
FIG. 37 is a set of photographs illustrating the effect of *Osteomeles schwerinae* extract on Muller cell activity in type II diabetes animal model (SDT).
Figure 38:
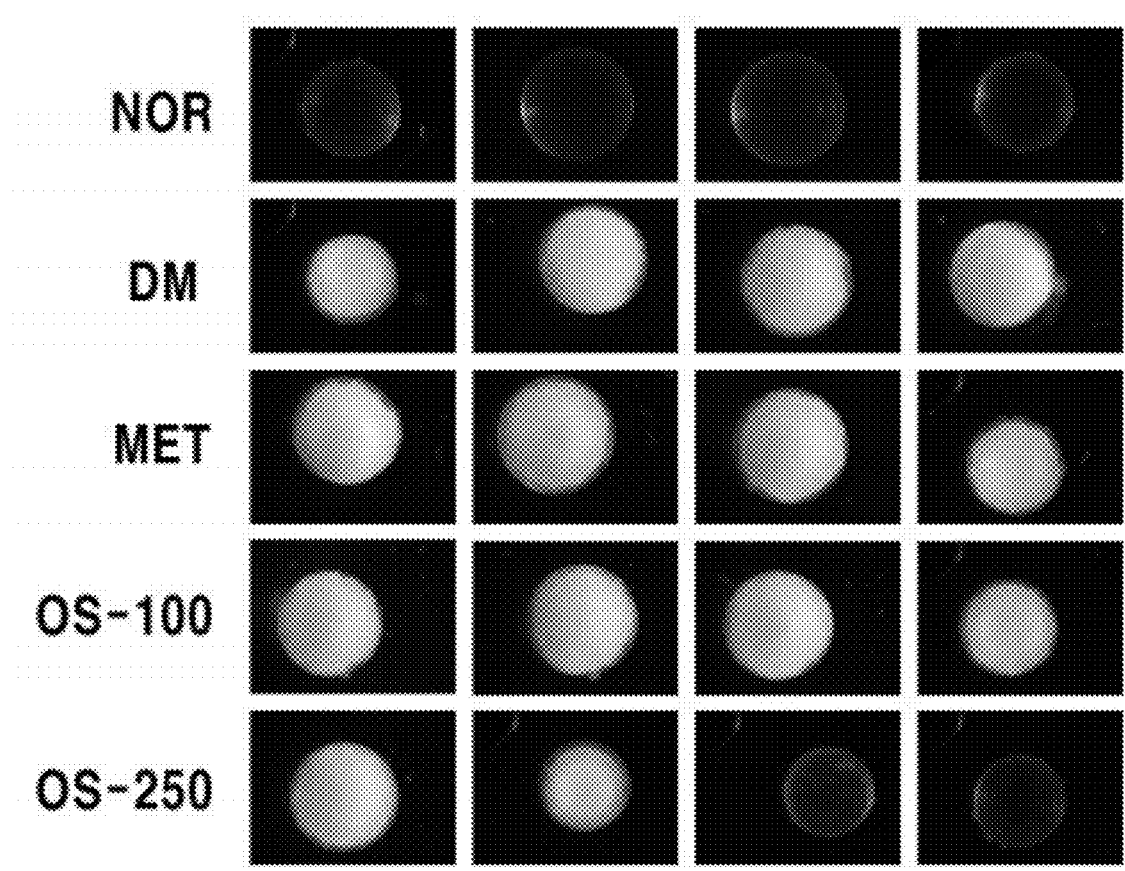
FIG. 38 is a set of photographs illustrating the preventive effect of *Osteomeles schwerinae* extract on lens opacity in type II diabetes animal model (SDT).

Muller cells are glial cells existing in retina, which support neuronal tissues. Glial cells are functioning to provide necessary materials to neurons and to create chemical environment appropriate for neuronal activity. In particular, once neurons in retina are damaged under high blood glucose condition, Muller cells are activated to be differentiated into multipotent progenitor cells, and at this time, specific marker GFAP is expressed. Therefore, the activation of Muller cells in retinal damage by diabetes can be confirmed by GFAP staining. As shown in FIG. 37, GFAP positive reaction was increase in the diabetes group, unlike the normal group. The GFAP positive reaction was rather decreased in the group treated with metformin, compared with the diabetes group. However, in the group treated with *Osteomeles schwerinae* extract, the GFAP positive reaction was significantly reduced. That is, the Muller cell activation was significantly inhibited in the group treated with *Osteomeles schwerinae* extract (see FIG. 37).

<5-2-4> Treatment and Postponement Effect on Diabetic Cataract

1. Preventive Effect on Lens Opacity

Figure 39:
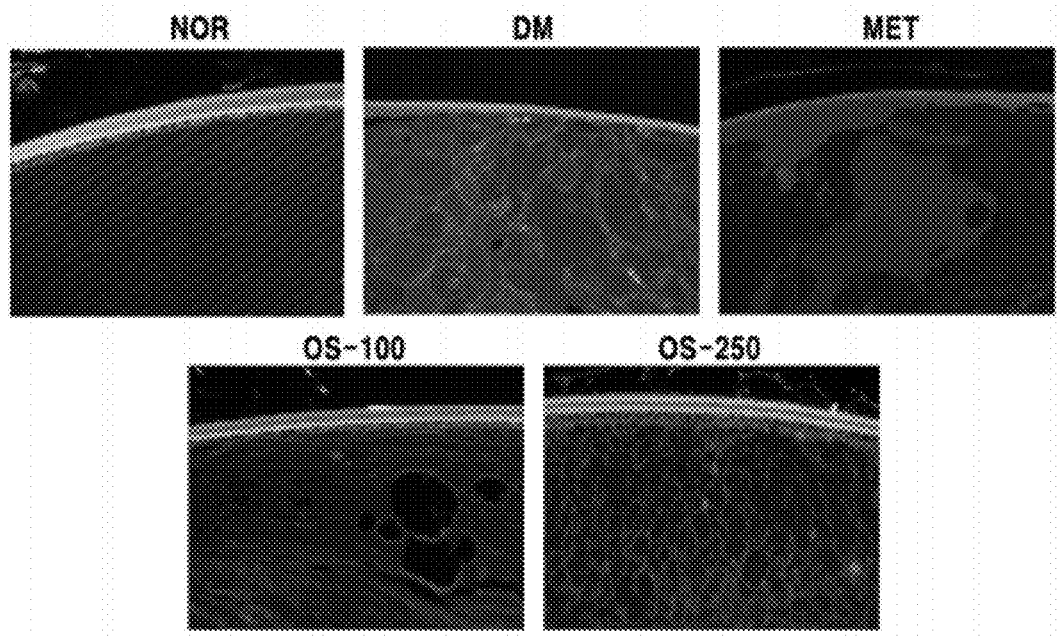
FIG. 39 is a set of photographs illustrating the preventive effect of *Osteomeles schwerinae* extract on lens fiber degeneration in type II diabetes animal model (SDT).

Lens was separated and lens opacity was examined to investigate the preventive effect of the extract on lens opacity. Eye balls were extracted during autopsy, which were placed in PBS (phosphate buffered saline, pH 7.4). Lens was carefully separated from the eyeball by posterior approach. Then, iris and zonule were eliminated. The lens was photographed under optical microscope equipped with CCD camera (BX51, Olympus, Japan). Lens opacity was measured with the photographed lens images by using Scion image analyzer (Scion Corporation, USA). The results of investigation of lens opacity with the lens isolated from the eye ball extracted during autopsy are shown in FIG. 39 and in FIG. 40. Lens opacity was not observed in the normal group (NOR), while the severe overall lens opacity and even opaque lens nucleus were observed in the diabetes group (DM). Lens opacity observed in the group treated with the control drug metformin (MET) was similar to that of the diabetes group. However, in the group treated with high concentration (250 mg/kg) of *Osteomeles schwerinae* extract, lens opacity was inhibited. Incidence rate of cataract and lens opacity were quantitatively analyzed. As a result, lens opacity was inhibited in all the groups treated with the sample drug (see FIG. 38).

2. Preventive Effect on Lens Fiber Degeneration

Lens opacity is caused by the degeneration of lens fiber composing lens. Thus, to investigate the effect of *Osteomeles schwerinae* extract on lens fiber degeneration, the effect of *Osteomeles schwerinae* extract on lens fiber degeneration in SDT type II diabetes rat was analyzed. To observe the degeneration of lens fiber induced by cataract, lens was fixed in 10% neutralized formalin (Microme, USA) for 24 hours, followed by the conventional tissue treatment. After paraffin embedding, the embedded block was cut into 2 μm thick sections, followed by hydration. The sections were stained with rhodamine-labeled wheat-germ agglutinin (WGA, Vector Laboratory, USA), and observed under fluorescent microscope (BX51, Olympus, Japan). To investigate the preventive effect on lens fiber degeneration, lens was stained and observed. As a result, as shown in FIG. 32, the arrangement of lens fiber was evenly distributed in the normal group. However, in the diabetes group, significant swelling and vesicle formation of lens fiber were observed. In the group treated with metformin, improving effect was hardly observed, like the diabetes group. In the group treated with high concentration of *Osteomeles schwerinae* extract, light swelling was observed, but vesicle formation was inhibited dose-dependently (see FIG. 39).

2. Measurement of Aldose Reductase Activity in Lens

Figure 40:
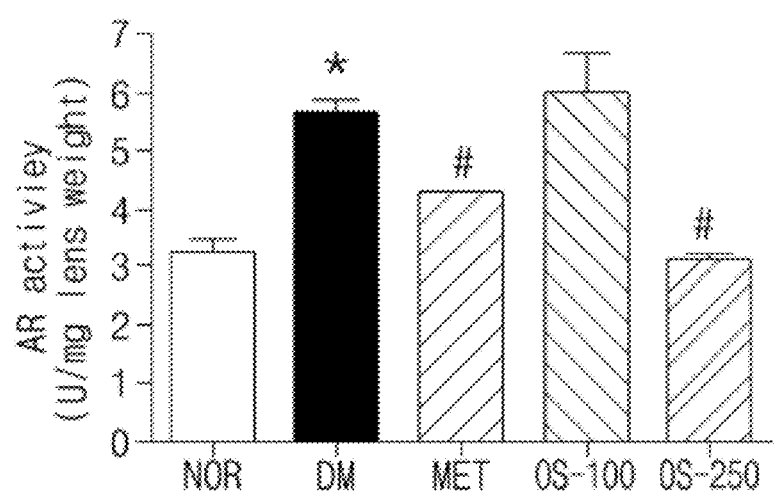
FIG. 40 is a graph illustrating the effect of *Osteomeles schwerinae* extract on aldose reductase activity in lens in type II diabetes animal model (SDT).

To obtain aldose reductase from lens, the lens was pulverized by using 135 mM Na, K-phosphate buffer (pH 7.0), and 10 mM 2-mercaptoethanol. After performing centrifugation at 14000 rpm for 30 minutes, the supernatant was filtered with 0.2 μm filter. The separated protein was quantified by Lowry method. 135 mM Na, K-phosphate buffer (pH 7.0), 100 mM Lithium sulfate, 0.03 mM NADPH and 0.04 mM DL-glyceraldehyde were all mixed together with 100 μg/ml of the supernatant to make the final volume of the mixture 1 ml. After adding the supernatant, level of NADPH, the substrate, was measured at 340 nm 0, 10, 20, and 30 minutes later, respectively. The results of the investigation of aldose reductase (AR) activity in lens are shown in FIG. 40. AR activity was significantly increased in the diabetes group, while AR activity was significantly reduced in the groups treated with metformin and 250 mg/ml of *Osteomeles schwerinae* extract, compared with the diabetes group. Such inhibitory effect was significant in the group treated with high concentration of *Osteomeles schwerinae* extract (see FIG. 40). From the above results, it was confirmed that the *Osteomeles schwerinae* extract of the present invention inhibits the generation, accumulation or expression of advanced glycation endproducts (AGEs) and RAGEs (receptor of advanced glycation end products) in retina, lens and renal tissues, and inhibits abnormal activation of aldose reductase, the first enzyme of polyol pathway, and at the same time has excellent anti-oxidative effect. In addition, the *Osteomeles schwerinae* extract of the present invention was confirmed to be very effective in the inhibition of early progress of renal complications since the extract has the effect of preventing the degeneration of lens fiber, delaying the development of cataract, preventing pericyte loss and acellular capillary formation in retina, preventing retinal angiogenesis and blood-retinal barrier breakage, preventing apoptosis of retinal blood vessel cells, inhibiting abnormal activation of Muller cells, preventing podocyte loss in the surface of kidney, and reducing the proliferation of glomerular mesangium.

INDUSTRIAL APPLICABILITY

The present invention relates to a natural extract which is effective in treating diabetic complications, and effective in anti-aging because it has anti-oxidative activity. Therefore, the extract of the present invention not only can be effectively used as a pharmaceutical composition for the prevention of diabetic complications and aging but also can be applied to a functional health food.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for treatment of a diabetic complication comprising:
administering a pharmaceutically effective dose of a composition comprising an extract of *Osteomeles schwerinae* or a fraction thereof as an active ingredient to a subject having diabetes, wherein the diabetic complication is selected from the group consisting of diabetic nephropathy, diabetic retinopathy, and diabetic cataract; wherein the extract is prepared by extracting *Osteomeles schwerinae* with ethanol or aqueous ethanol as an extracting solvent, and wherein the fraction is obtained by systematic sequential fractionation of the *Osteomeles schwerinae* extract using hexane, ethyl acetate, butanol and water in that order.

2. The method according to claim 1, wherein the extract is obtained from the twigs, leaves or seeds of *Osteomeles schwerinae*.

3. The method according to claim 1, wherein the fractions contains 2"-O-acetylvitexin, hyperoside or quercitrin.

4. The method according to claim 1, wherein the fraction is obtained by:
i) removing ethanol or aqueous ethanol solvent from the ethanol or aqueous ethanol extract of *Osteomeles schwerinae* to obtain a crude extract product;
ii) adding water and hexane to the extract product obtained from step (i), separating a first water layer and hexane layer and removing hexane from the hexane layer to obtain a hexane fraction;
iii) adding ethyl acetate to the first water layer obtained from step (ii), separating a second water layer and ethyl acetate layer and removing ethyl acetate from the ethyl acetate layer to obtain an ethyl acetate fraction;
iv) adding butanol to the second water layer obtained from step (iii), separating a third water layer and butanol layer and removing butanol from the butanol layer to obtain a butanol fraction; and
v) removing water from the third water layer obtained from step (iv) to obtain a water fraction.

\* \* \* \* \*